United States Patent
Nonaka et al.

(12) 
(10) Patent No.: US 10,492,748 B2
(45) Date of Patent: Dec. 3, 2019

(54) RADIATION IMAGING APPARATUS AND CONTROL METHOD THEREFOR

(71) Applicant: CANON KABUSHIKI KAISHA, Tokyo (JP)

(72) Inventors: Hideki Nonaka, Yokohama (JP); Taro Hiroike, Yamato (JP); Asato Kosuge, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 359 days.

(21) Appl. No.: 15/584,105

(22) Filed: May 2, 2017

(65) Prior Publication Data
US 2017/0332987 A1    Nov. 23, 2017

(30) Foreign Application Priority Data
May 17, 2016 (JP) .................. 2016-099049

(51) Int. Cl.
*A61B 6/00* (2006.01)

(52) U.S. Cl.
CPC ............. *A61B 6/46* (2013.01); *A61B 6/4266* (2013.01); *A61B 6/5205* (2013.01); *A61B 6/5258* (2013.01)

(58) Field of Classification Search
CPC ....... A61B 6/4266; A61B 6/46; A61B 6/5205; A61B 6/5258
See application file for complete search history.

(56) References Cited

U.S. PATENT DOCUMENTS

| | | | |
|---|---|---|---|
| 6,144,876 A * | 11/2000 | Bouton | A61B 6/4258 600/436 |
| 2001/0052572 A1 * | 12/2001 | Mikami | G01T 1/00 250/394 |
| 2004/0258204 A1 | 12/2004 | Nokita et al. | 378/91 |

FOREIGN PATENT DOCUMENTS

JP    A 2005-013272    1/2005

* cited by examiner

*Primary Examiner* — Chih-Cheng Kao
(74) *Attorney, Agent, or Firm* — Venable LLP

(57) ABSTRACT

A radiation imaging apparatus includes a sensor unit in which a plurality of detecting elements each configured to detect emitted radiation are arranged, and a notification unit configured to make a notification by a sound. As the sound produced from the notification unit, a sound having a fundamental frequency which satisfies a condition determined based on the number of rows of a predetermined area of an image read out from the sensor unit and a readout frequency of signals of each row is used.

16 Claims, 16 Drawing Sheets

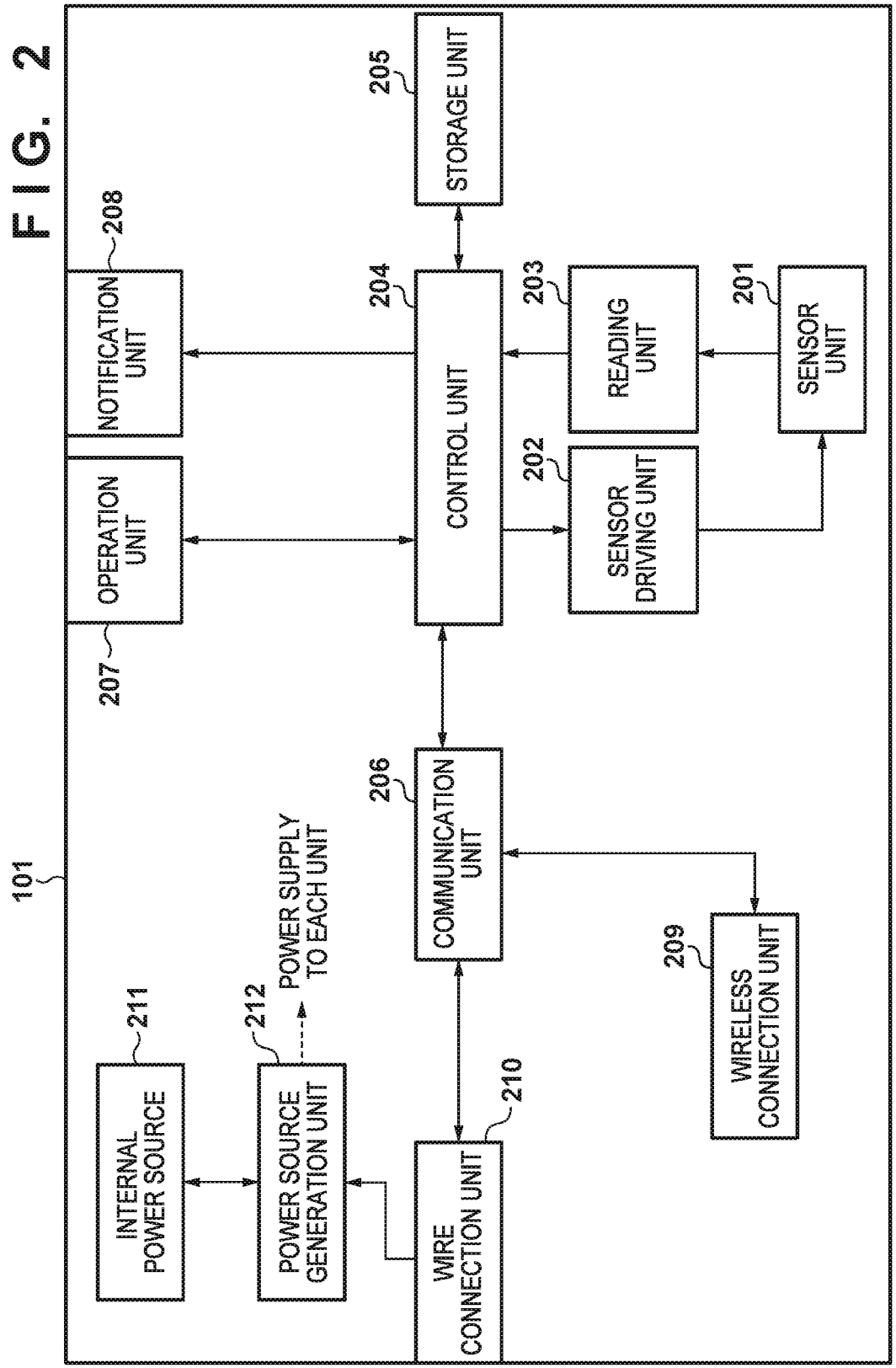

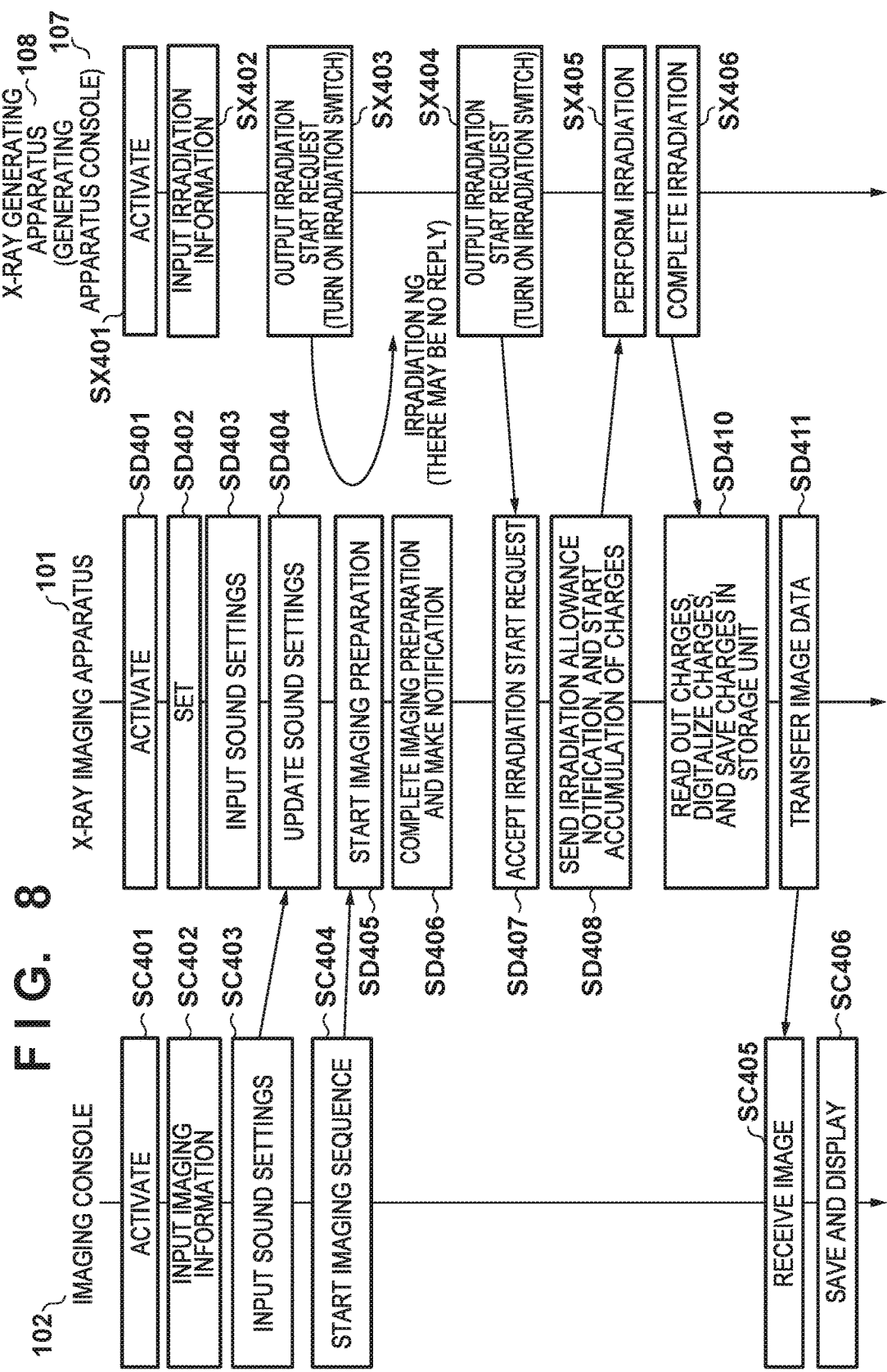

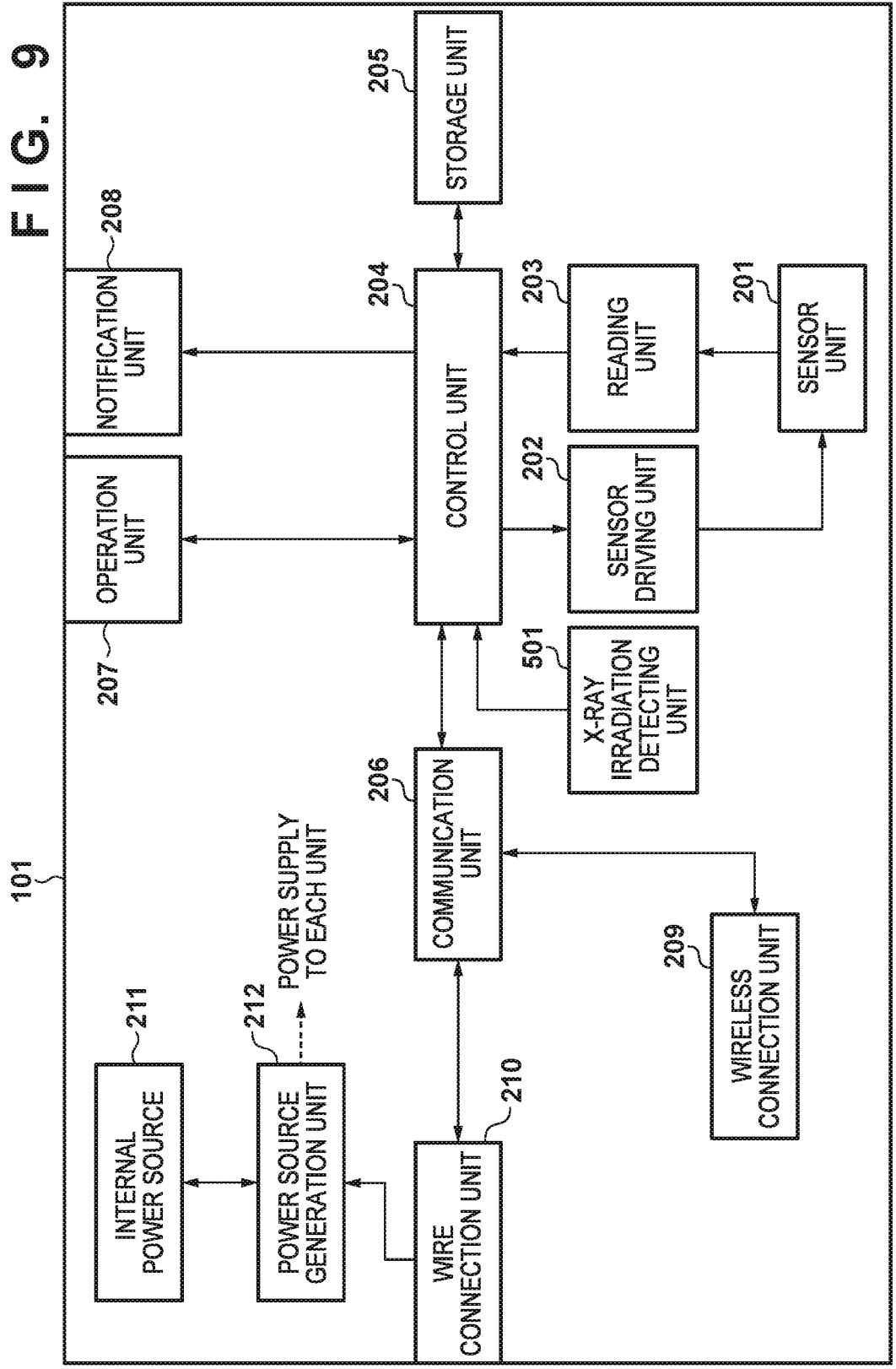

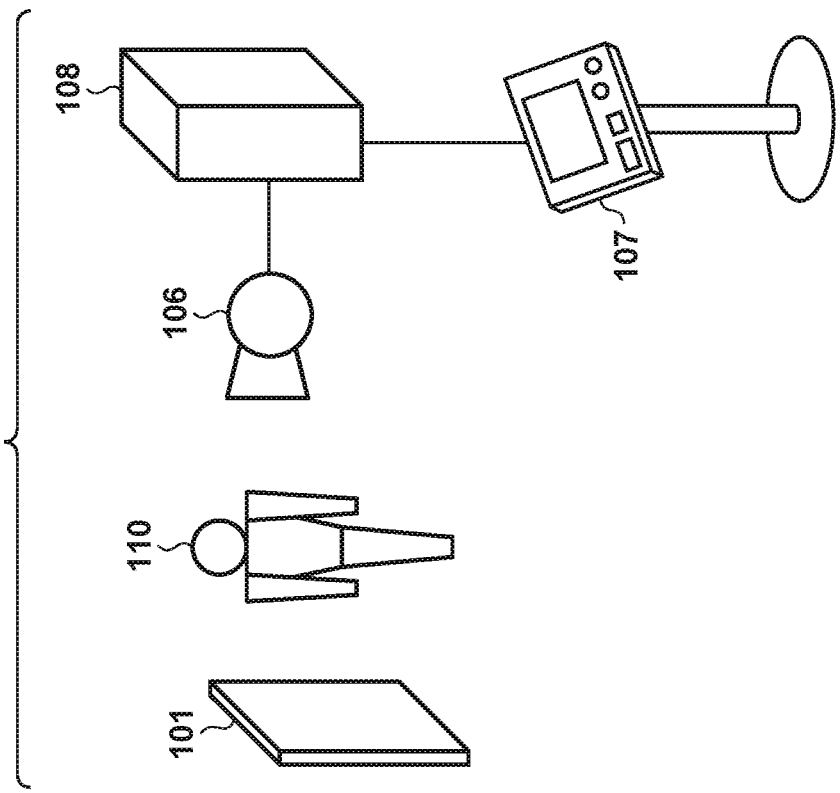
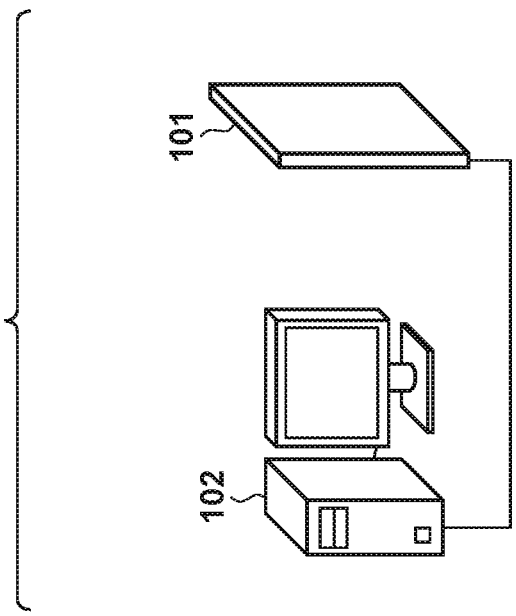
F I G. 13B
F I G. 13A

RADIATION IMAGING APPARATUS AND CONTROL METHOD THEREFOR

BACKGROUND OF THE INVENTION

Field of the Invention

The present invention relates to a radiation imaging apparatus and a control method therefor.

Description of the Related Art

Conventionally, an X-ray imaging apparatus which detects the intensity distribution of X-rays generated by an X-ray source and transmitted through an object and converts it into an image or an X-ray imaging system including the apparatus has become commercially available. As methods of obtaining an image by the X-ray imaging apparatus, a method using a dedicated film and a method (electrical method) of converting X-rays into visible light by a phosphor, converting the visible light into an electrical signal by a photosensor, and obtaining digital image data are known.

The main body of an X-ray imaging apparatus using the electrical method may be provided with a notification function for notifying the user of the state of the apparatus. A practical example of the notification function is a function using light or a sound. Japanese Patent Laid-Open No. 2005-013272 proposes an X-ray imaging apparatus which implements a notification function by mounting or connecting a light emitting component such as an LED or lamp or a sound-production component such as a loudspeaker. The notification function allows the user to recognize information about the state or operation of the X-ray imaging apparatus, for example, whether the X-ray imaging apparatus is active, or whether the X-ray imaging apparatus can capture an X-ray image.

To provide a notification function using a sound in the X-ray imaging apparatus, it is considered to mount a sound-production component such as a loudspeaker. The sound-production component such as a loudspeaker generates electromagnetism during a sound-production period. In general, a component driven by electricity generates electromagnetism during driving. Since a sound-production component like a loudspeaker includes a component such as a coil which is intended to generate electromagnetism, the intensity of generated electromagnetism may be higher than that of other components. On the other hand, the X-ray imaging apparatus is provided with a sensor or detection mechanism with high sensitivity, such as a photoelectric conversion sensor array or a mechanism for X-ray irradiation detection. Therefore, in the X-ray imaging apparatus, an electromagnetic influence may be exerted on the detection mechanism or sensor by driving the sound-production component, thereby causing image noise or an operation error.

SUMMARY OF THE INVENTION

According to an embodiment of the present invention, there are provided a radiation imaging apparatus which reduces the influence of driving of a sound-production component on an image and/or imaging operation, and a control method for the apparatus.

According to one aspect of the present invention, there is provided a radiation imaging apparatus comprising: a sensor unit in which a plurality of detecting elements each configured to detect emitted radiation are arranged; and a notification unit configured to make a notification by a sound, wherein the sound produced from the notification unit has a fundamental frequency based on a readout frequency of signals in the sensor unit.

According to another aspect of the present invention, there is provided a radiation imaging apparatus comprising: a sensor unit in which a plurality of detecting elements each configured to detect emitted radiation are arranged; a notification unit configured to make a notification by a sound; and a detecting unit configured to detect radiation irradiation to the sensor unit by sampling a current value flowing through a bias wiring connected to the plurality of detecting elements of the sensor unit, wherein a fundamental frequency of a sound produced from the notification unit satisfies a condition of being not higher than ½ of a frequency of sampling of the current value performed by the detecting unit.

According to another aspect of the present invention, there is provided a radiation imaging apparatus comprising: a sensor unit in which a plurality of detecting elements each configured to detect emitted radiation are arranged; a notification unit configured to make a notification by a sound; and a detecting unit configured to detect radiation irradiation to the sensor unit by sampling a current value flowing through a bias wiring of the sensor unit, wherein the detecting unit includes a bandpass filter for reducing noise, and a condition given by $$fa < fl \text{ or } fa > fh \text{ for } fa \leq fs/2$$

$$fs - fa < fl \text{ or } fs - fa > fh \text{ for } fa > fs/2$$

is satisfied where fa represents a fundamental frequency of the sound produced from the notification unit, fs represents a frequency of sampling by the detecting unit, and fl to fh represent a frequency band which the bandpass filter passes.

According to another aspect of the present invention, there is provided a control method for a radiation imaging apparatus including a sensor unit in which a plurality of detecting elements each configured to detect emitted radiation are arranged, and a notification unit configured to make a notification by a sound, the method comprising: detecting occurrence of an event to be notified; and causing the notification unit to execute sound production in response to the detection of the occurrence of the event, wherein the sound produced from the notification unit has a fundamental frequency based on a readout frequency of signals in the sensor unit.

According to another aspect of the present invention, there is provided a computer-readable medium storing a program for causing a computer of a radiation imaging apparatus including a sensor unit in which a plurality of detecting elements each configured to detect emitted radiation are arranged, and a notification unit configured to make a notification by a sound, to execute a control method, the method comprising: detecting occurrence of an event to be notified; and causing the notification unit to execute sound production in response to the detection of the occurrence of the event, wherein the sound produced from the notification unit is based on a readout frequency of signals in the sensor unit.

Further features of the present invention will become apparent from the following description of exemplary embodiments (with reference to the attached drawings).

BRIEF DESCRIPTION OF THE DRAWINGS

FIG. 2 is a block diagram showing an example of the arrangement of an X-ray imaging apparatus according to the first embodiment;

FIG. 8 is a flowchart for explaining processing between apparatuses at the time of the synchronization mode;

FIG. 9 is a block diagram showing an example of the arrangement of an X-ray imaging apparatus according to the second embodiment;

FIGS. 13A and 13B are views each showing an example of the arrangement of an X-ray imaging system at the time of a console-less mode.

DESCRIPTION OF THE EMBODIMENTS

Embodiments of the present invention will be described below with reference to the accompanying drawings. Note that in each of the following embodiments, an X-ray imaging system and an X-ray imaging apparatus, which use X-rays as radiation, will be exemplified. However, an imaging system and an imaging apparatus, which use radiation other than X-rays, may be adopted.

First Embodiment

Figure 1:
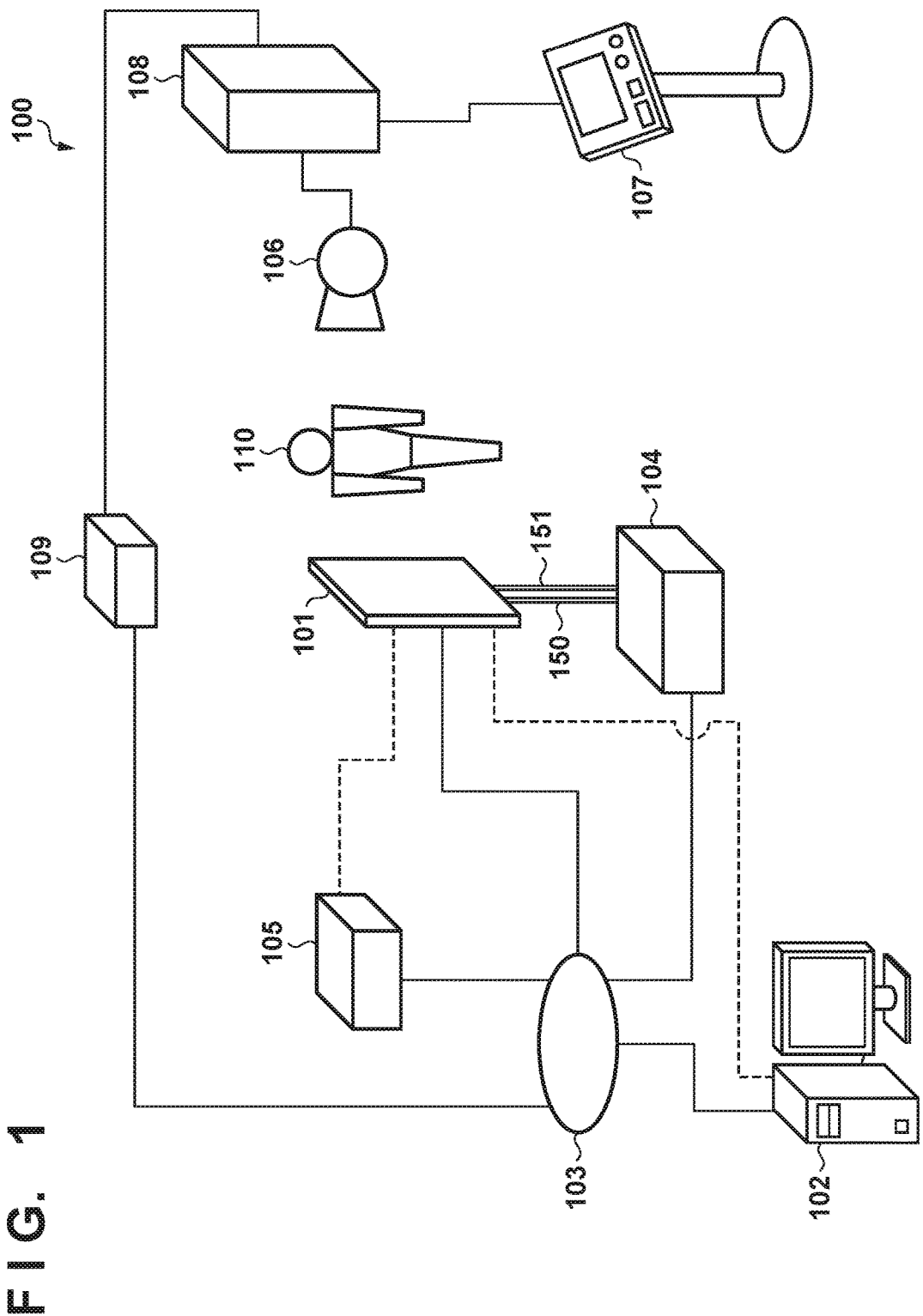
FIG. 1 is a view showing an example of the arrangement of an X-ray imaging system according to embodiments.

In the first embodiment, a case in which an X-ray imaging system operates in a synchronization mode will be described. In the synchronization mode, an X-ray imaging apparatus and an X-ray generating apparatus capture an image in synchronism with each other by communication between the X-ray imaging apparatus and the X-ray generating apparatus. An example will be explained below in which the influence of sound-production driving of a sound-production unit on a captured image is reduced by limiting, based on the readout frequency of signals in a sensor unit, the fundamental frequency of a sound output from the sound-production unit provided in the X-ray imaging apparatus. FIG. 1 shows an example of the arrangement of an X-ray imaging system 100 according to the first embodiment. The arrangement of the X-ray imaging system 100 according to the first embodiment will be described below with reference to FIG. 1.

An X-ray imaging apparatus 101 serving as a radiation imaging apparatus has one or both of a wire communication function and a wireless communication function. The X-ray imaging apparatus 101 can exchange data with an imaging console 102 via a communication path. The imaging console 102 is constructed by, for example, a computer apparatus (a PC or the like) having a display function such as a monitor and a function of accepting an input instruction from the user (radiographer or operator). The imaging console 102 can send, to the X-ray imaging apparatus 101, an instruction from the user, or receive an image acquired by the X-ray imaging apparatus 101 and present it to the user. Furthermore, the imaging console 102 has one or both of a wire communication function and a wireless communication function. Note that FIG. 1 shows an example in which the imaging console 102 is of a stationary type. However, no such restriction is imposed on an actual operation, and a notebook PC, tablet device, or the like of a portable type may be used as the imaging console 102.

The X-ray imaging apparatus 101 sends an acquired X-ray image to the imaging console 102. The X-ray image may be sent from the X-ray imaging apparatus 101 to the imaging console 102 via a LAN 103 or may be directly sent from the X-ray imaging apparatus 101 to the imaging console 102. For example, the LAN 103 is formed by a wire cable. The LAN 103 is connected to the X-ray imaging apparatus 101 and the imaging console 102, thereby allowing exchange of data such as an X-ray image between the X-ray imaging apparatus 101 and the imaging console 102.

Furthermore, the X-ray imaging apparatus 101 may have a power receiving function together with a connection for wire communication. In this case, by connecting, to the X-ray imaging apparatus 101, a power source unit 104 which can implement power supply and communication at the same time, the power source unit 104 can supply power to the X-ray imaging apparatus 101 while mediating communication between the X-ray imaging apparatus 101 and the imaging console 102. Referring to FIG. 1, lines 150 and 151 each connecting the X-ray imaging apparatus 101 and the power source unit 104 indicate a communication wiring and a power supply wiring, respectively. These two wirings may be accommodated in one cable or separately prepared. FIG. 1 shows a state in which the power source unit 104 is connected to the LAN 103. However, the power source unit 104 and the imaging console 102 may be directly connected.

If the X-ray imaging apparatus 101 communicates with the imaging console 102 by wireless communication, it may be connected to the LAN 103 via an access point (AP 105). Note that FIG. 1 shows a state in which the AP 105 is connected to the LAN 103 but the AP 105 and the imaging console 102 may be directly connected. Furthermore, the X-ray imaging apparatus 101 and the imaging console 102 may have a function of directly exchanging data with each other via wireless or wire communication. In this case, the X-ray imaging apparatus 101 may have the function of the AP 105. An example of the communication path when the X-ray imaging apparatus 101 and the imaging console 102 exchange data has been explained.

Referring to FIG. 1, an X-ray generating apparatus 108 is connected to an X-ray tube 106 for generating X-rays, an X-ray generation console 107 for accepting a user operation such as an X-ray generation instruction, and a connection device 109 for performing communication connection to the LAN 103. The X-ray generating apparatus 108 and the X-ray imaging apparatus 101 can be communicably connected via the connection device 109 and the LAN 103. The X-ray imaging apparatus 101 implements the synchronization mode of synchronizing an imaging operation and an X-ray irradiation operation by the X-ray generating apparatus 108 by communication via the connection.

The procedure of X-ray imaging of an object 110 by the X-ray imaging system 100 will now be described. To perform X-ray imaging of the object 110, the user arranges the X-ray imaging apparatus 101 at a position where it is irradiated with X-rays emitted by the X-ray tube 106 and transmitted through the object 110. Next, the user activates the X-ray imaging apparatus 101. The user operates the imaging console 102 to set the X-ray imaging apparatus 101 in an imaging enable state. Subsequently, the user operates the X-ray generation console 107 to set X-ray irradiation conditions. After the end of the above-described operation, the user confirms that imaging preparation including the object 110 is completed, and the user presses an exposure switch provided on the X-ray generation console 107, thereby instructing the X-ray generating apparatus 108 to perform X-ray exposure.

Upon accepting the X-ray exposure instruction, the X-ray generating apparatus 108 notifies the X-ray imaging apparatus 101 of a signal indicating that X-ray irradiation starts via the connection device 109 and the LAN 103. Note that in FIG. 1, the X-ray imaging apparatus 101 and the X-ray generating apparatus 108 are connected via the connection device 109 and the LAN 103. However, the connection form is not limited to this. For example, the X-ray generating apparatus 108 and the X-ray imaging apparatus 101 may be directly connected without intervention of the connection device 109 and the LAN 103. If the X-ray imaging apparatus 101 has a function of detecting X-ray irradiation, and the X-ray imaging apparatus 101 operates in an X-ray irradiation detection mode (to be described later in the second embodiment), the X-ray generating apparatus 108 need not notify the X-ray imaging apparatus 101 of irradiation.

Upon receiving, from the X-ray generating apparatus 108, the signal indicating that X-ray irradiation starts, the X-ray imaging apparatus 101 confirms whether it is ready for X-ray irradiation. If there is no problem, the X-ray imaging apparatus 101 replies with irradiation allowance to the X-ray generating apparatus 108. Upon receiving the irradiation allowance from the X-ray imaging apparatus 101, the X-ray generating apparatus 108 drives the X-ray tube 106 to perform X-ray irradiation. Upon detecting the end of X-ray irradiation, the X-ray imaging apparatus 101 starts generating an X-ray image. The X-ray imaging apparatus 101 sends the generated X-ray image to the imaging console 102 via the above-described communication path. Note that the end of X-ray irradiation can be detected by various methods, for example, a notification from the X-ray generating apparatus 108 or detection of a lapse of a predetermined irradiation time. The imaging console 102 stores the data (X-ray image) received from the X-ray imaging apparatus 101 or displays it on a display unit.

The arrangement of the X-ray imaging apparatus 101 will be described next with reference to FIG. 2. In the X-ray imaging apparatus 101, a housing accommodates a sensor unit 201 in which a plurality of detecting elements each for detecting emitted radiation and which includes a sensor array for generating a signal corresponding to X-rays, and a notification unit 208 including a sound-production unit for making a notification by sound reproduction. The sensor unit 201 according to this embodiment has a form in which a detecting element for detecting light is arranged under a fluorescent substance (scintillator) layer, as will be described later. Note that a detecting element in a form of directly converting radiation into an electrical signal may be used. In any form, the detecting element functions as a detecting element for detecting emitted radiation, and will be referred to as a radiation detecting element hereinafter. Note that the notification unit 208 may be connectable to the housing. In the X-ray imaging apparatus 101, the sensor unit 201 changes incident X-rays into an electrical signal. The sensor unit 201 is formed by the scintillator (not shown) and a detector array. Details of the detector array will be described with reference to FIG. 11. The scintillator and the detector array have two-dimensional planar shapes and are adjacent to each other so that the planes face each other. The scintillator is excited by radiation such as X-rays and generates visible light. Charges corresponding to the period and the intensity of the light are accumulated in the respective pixels of the detector array. Note that the arrangement of the sensor unit 201 is not limited to this, and a direct conversion type sensor for directly converting X-rays into an electrical signal may be used.

A control unit 204 drives a sensor driving unit 202 and a reading unit 203 so as to implement sequential scanning of the detector array. This sequential scanning causes the reading unit 203 to sequentially read out signals from the sensor unit 201 in cooperation with the sensor driving unit 202 for each row of the detector array. The reading unit 203 converts signals into digital information. When extracting charges accumulated in the detector array, the control unit 204 instructs the sensor driving unit 202 to select a specific row of the detector array to extract charges. The sensor driving unit 202 drives a row selection unit 1132 shown in FIG. 11 to sequentially drive switch elements 1135, thereby sequentially selecting rows Lr1 to Lr4096. The reading unit 203 reads out signals from photoelectric conversion elements 1021 serving as radiation detecting elements, which are connected to the selected row of the detector array. The reading unit 203 amplifies signals, thereby performs digitalization. The data digitalized by the reading unit 203 is sent to the control unit 204, and stored by the control unit 204 as an X-ray image in a storage unit 205. Using a communication function (communication unit 206), the control unit 204 externally sends the X-ray image stored in the storage unit 205. Note that the externally sent X-ray image is the X-ray image stored in the storage unit 205 or the X-ray image having undergone some processing. In some cases, the X-ray image remains in the storage unit 205 without being externally sent.

The control unit 204 includes, for example, a memory and a CPU as a processor. The control unit 204 performs processing associated with control of each unit of the X-ray imaging apparatus 101 by executing, by the CPU, a program stored in the memory. For example, the control unit 204 outputs, to the sensor driving unit 202, an instruction to drive the sensor unit 201 for imaging. The control unit 204 saves, in the storage unit 205, the X-ray image read out by the reading unit 203 from the sensor unit 201. The control unit 204 reads out the X-ray image saved in the storage unit 205. The control unit 204 also sends the X-ray image to another apparatus via the communication unit 206. The control unit 204 receives an instruction from an external apparatus via the communication unit 206. The control unit 204 switches activation/stop of the X-ray imaging apparatus 101 in response to an operation from an operation unit 207. The control unit 204 also controls to notify the user of the operation status or error state of the X-ray imaging apparatus 101 by light or a sound using the notification unit 208. Note that the above-described processing contents are processed by one control unit 204 in this embodiment. However, a plurality of control units 204 may be provided to share the processing. As for practical implementation of the control unit 204, a CPU (Central Processing Unit), a MPU (Micro Processing Unit), an FPGA (Field-Programmable Gate Array), a CPLD (Complex Programmable Logic Device), or the like can be used, and the present invention is not particularly limited.

The storage unit 205 is used to save the X-ray image acquired by the X-ray imaging apparatus 101, or log information indicating an internal processing result or the like. If the control unit 204 is a component using software, such as a CPU, the storage unit 205 can store a program for it. Note that practical implementation of the storage unit 205 is not limited, and the storage unit 205 can be implemented by various combinations of semiconductor memories, HDDs, and volatile/nonvolatile memories. This embodiment illustrates only one storage unit 205. However, a plurality of storage units 205 can be arranged.

The communication unit 206 performs processing for implementing communication between the X-ray imaging apparatus 101 and another apparatus. The communication unit 206 according to this embodiment is connected to a wireless connection unit 209 for wireless communication. The communication unit 206 can communicate with the AP 105 or the imaging console 102 via the wireless connection unit 209. An example of the wireless connection unit 209 is an antenna for wireless communication. The communication unit 206 is connected to a wire connection unit 210. The communication unit 206 can communicate with the power source unit 104 or the imaging console 102 via the wire connection unit 210. The wire connection unit 210 has a mechanism capable of receiving power when connected to the power source unit 104. An example of the mechanism is a connector including a communication pin and a power source pin. The wire connection unit 210 having such mechanism implements wire communication and reception of power supply using the power source unit 104. Note that the communication unit 206 is not limited to the above arrangement. The communication unit 206 may have an arrangement including only the wire communication function or the wireless communication function. The standard and method of the communication are not particularly limited.

The X-ray imaging apparatus 101 includes an internal power source 211. In this embodiment, the internal power source 211 is a rechargeable battery. The internal power source 211 is detachable from the main body of the X-ray imaging apparatus 101. The internal power source 211 is not limited to this example, and whether the internal power source 211 is rechargeable or unrechargeable, whether the internal power source 211 is detachable or undetachable, a power generation method, and the like are not limited.

A power source generation unit 212 generates a voltage/current needed by each unit of the X-ray imaging apparatus 101 from power given by the internal power source 211. The power source generation unit 212 distributes the voltage/current to each unit. While the X-ray imaging apparatus 101 is connected to the power source unit 104, the power source unit 104 supplies power to the power source generation unit 212 via the wire connection unit 210. The power source generation unit 212 can supply power to each unit of the X-ray imaging apparatus 101 using the power supplied from the power source unit 104. The power source generation unit 212 charges the internal power source 211.

The operation unit 207 is used to accept an operation from the user. The implementation method of the operation unit 207 is not particularly limited, and the operation unit 207 need only be configured to accept an input from the user. More specifically, the operation unit 207 can be implemented by various kinds of switches, a touch panel, and the like to be manually operated by the user. A reception unit for accepting an input from a dedicated remote controller may be provided in the operation unit 207.

The notification unit 208 is used to notify the user or the like of the state of the X-ray imaging apparatus 101 and the like. The notification unit 208 includes a light emitting unit for making a notification by light and a sound-production unit for making a notification by a sound. The implementation method of the notification unit 208 is not particularly limited. The light emitting unit can be implemented by an LED, an LCD monitor, or the like. The sound-production unit is implemented by a loudspeaker. The sound-production unit has a function of implementing various kinds of sound production. The X-ray imaging apparatus 101 according to this embodiment has a notification function (light emitting unit) such as an LED using light and a notification function (sound-production unit) such as loudspeaker using a sound.

Sound-production processing from the notification unit 208 by the X-ray imaging apparatus 101 having the above arrangement will be described with reference to flowcharts shown in FIGS. 3A and 3B.

Upon activation of the X-ray imaging apparatus 101, the control unit 204 is supplied with power and activated. In addition, other function units are supplied with power and activated. Note that at the time of activation of the X-ray imaging apparatus 101, not all the function units of the X-ray imaging apparatus 101 need to be activated. For example, the function units such as the sensor unit 201 used for imaging may not be activated before an imaging request is issued. Such activation control may be implemented by, for example, the control unit 204.

Figure 3A:
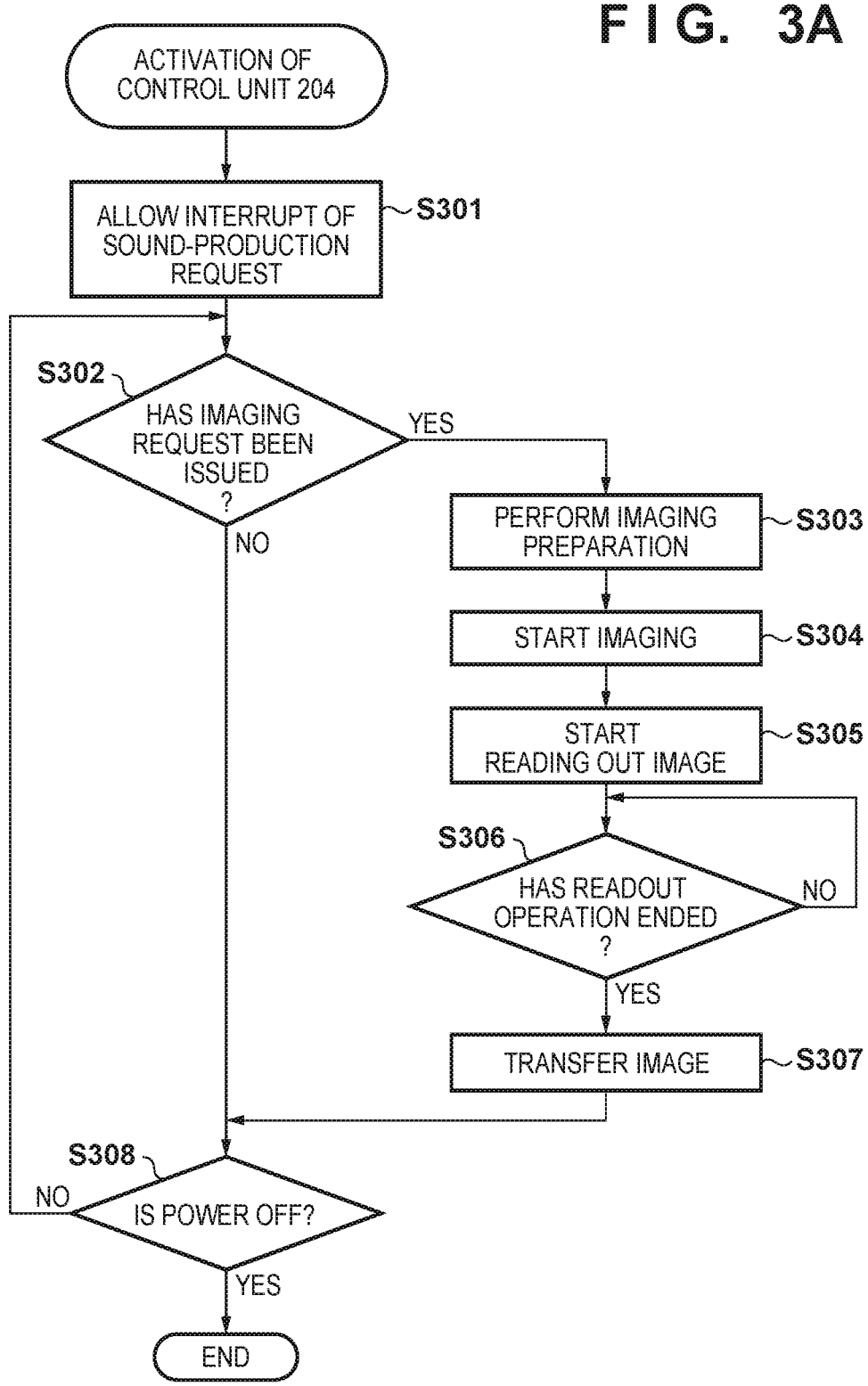
FIG. 3A is a flowchart illustrating X-ray imaging processing at the time of a synchronization mode.
Figure 3B:
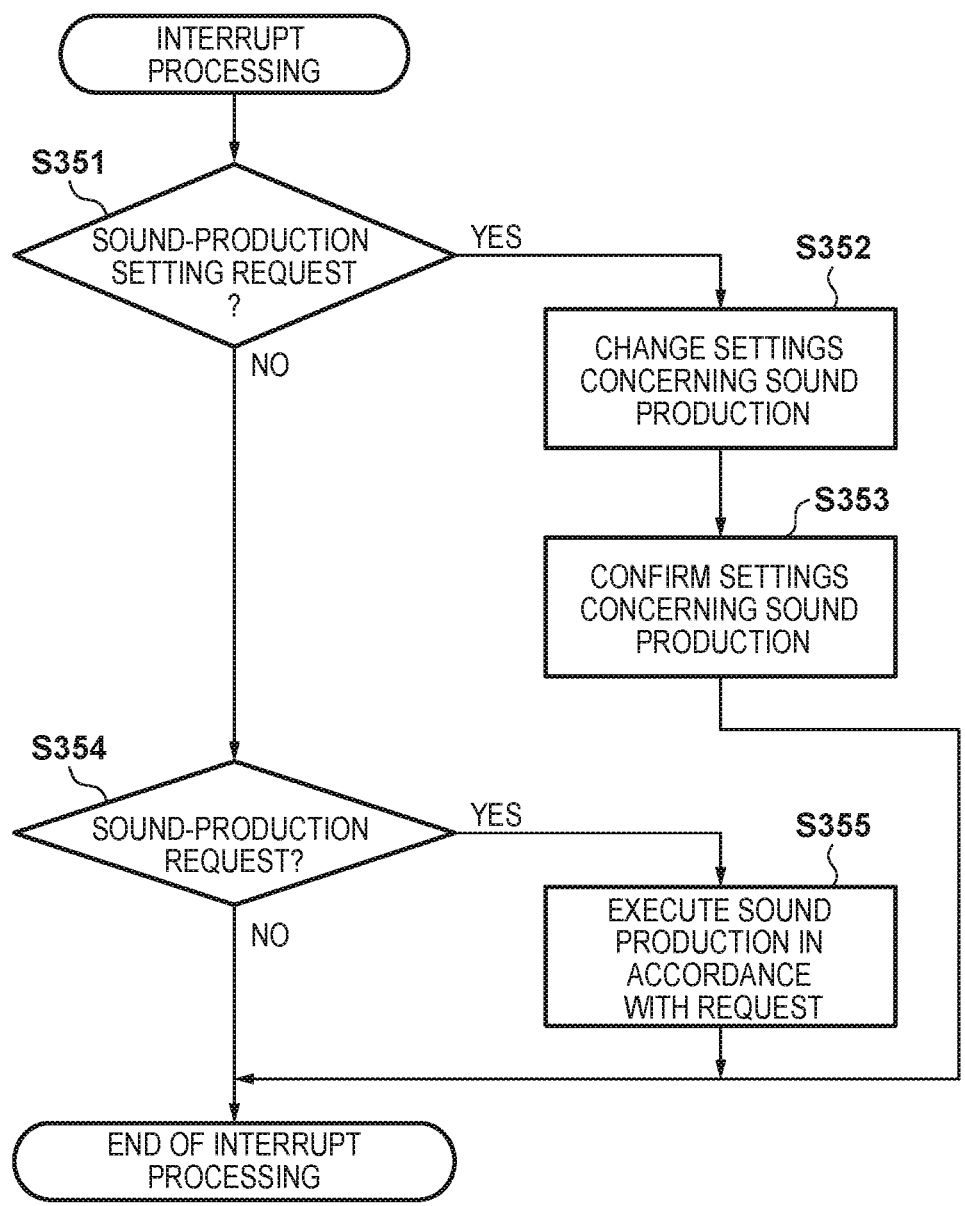
FIG. 3B is a flowchart illustrating interrupt processing associated with sound production.

As shown in FIG. 3A, upon activation, the control unit 204 allows an interrupt associated with sound production in step S301. If an interrupt associated with sound production is allowed, interrupt processing shown in FIG. 3B is executed in response to generation of an interrupt signal associated with sound production. The interrupt processing executed when an interrupt signal associated with sound production is generated will be described with reference to the flowchart of FIG. 3B.

When an interrupt signal associated with sound production is generated to start interrupt processing, the control unit 204 determines in step S351 whether the interrupt has been generated by a sound-production setting request. If it is determined that the interrupt has been generated by the sound-production setting request, the process advances to step S352; otherwise, the process advances to step S354. The sound-production setting request is a request to set ON/OFF of sound production by the sound-production unit, a volume, and the like, and includes setting information about sound production. In steps S352 and S353, the control unit 204 makes settings concerning sound production of the notification unit 208 based on the setting information included in the sound-production setting request.

Note that the setting request concerning sound production is generated in response to a user operation of changing sound-production settings, for example, an operation of turning on/off sound production, an operation of changing the volume, an operation of setting the correspondence between each of a plurality of events to be notified and a sound for notification. For example, the user can designate the correspondences between a plurality of types of sounds (tones, sound patterns, and the like) and respective events to be notified by sound production. An arrangement for accepting such user operation may be provided in one or both of the operation unit 207 of the X-ray imaging apparatus 101 and the imaging console 102. If, for example, an arrangement for a sound-production setting operation is provided in the operation unit 207 of the main body of the X-ray imaging apparatus 101, an operation input unit such as a switch or dial and a notification unit for notifying the user of an input result by light or a sound are preferably provided in the operation unit 207. It is possible to make sound-production settings and notify the user of a sound-production setting result (whether the current state is a sound-production state, and the degree of volume). Note that the notification unit may be implemented using the notification unit 208.

If a function of performing a sound-production setting operation is provided in the imaging console 102, for example, a method of displaying a setting target item on the display unit, and changing the sound-production settings by operating an instruction input unit such as a keyboard can be adopted. If sound-production settings are made from the imaging console 102, the setting information is transferred to the X-ray imaging apparatus 101 by communication. Based on the received setting information, the control unit 204 of the X-ray imaging apparatus 101 changes the sound-production settings and notifies the user of the setting result using the notification unit (notification unit 208), similarly to a case in which the sound-production settings are changed from the operation unit 207. As described above, in this embodiment, for example, an interrupt for setting sound production is generated when sound-production setting is instructed from the operation unit 207 or sound-production setting is instructed from the sound-production setting screen on the imaging console 102.

Note that a plurality of kinds of notifications using sounds are preferably prepared, as described above. This is because the number of states in which the X-ray imaging apparatus 101 makes a notification is larger than one. For example, if the X-ray imaging apparatus 101 is driven by a battery, it is easier to notify the user of the type of problem by differentiating a sound for notifying the user that the residual amount of the battery is small from a sound for notifying the user that wireless communication connection is impossible. As described above, it is preferable to provide a plurality of kinds of notifications using sounds. Thus, a method of identifying each state by adjusting combinations of tones and sound-production times to prepare a plurality of sounds or melodies is preferable instead of a short sound and sound production for a given time. The user can set the correspondence between a state to be notified and the type of sound or melody in the sound-production setting. Furthermore, a volume at the time of sound production can be set for each state to be notified.

If the settings concerning sound production are updated in step S352, the process advances to step S353. In step S353, the control unit 204 notifies the user of the sound-production setting result by causing the notification unit 208 to execute sound production in accordance with the settings updated in step S352. Note that in this embodiment, the sound-production setting result is confirmed after all the settings are made. The present invention, however, is not limited to this. For example, in an arrangement in which each state and a sound indicating each state can be individually set, a sound of a setting result may be confirmed every time the settings are changed. Alternatively, for example, when a sound-production test button provided in the operation unit 207 is operated, sound-production setting confirmation may be executed by interrupt processing. The setting result concerning sound production may be displayed in a visible form on a display unit provided in the notification unit 208 of the X-ray imaging apparatus 101 or the imaging console 102.

For example, a method of displaying, by ON/OFF of a specific LED, whether the function of producing a sound is ON or OFF may be used.

On the other hand, if it is determined in step S351 that the interrupt has not been generated by the sound-production setting request, the process advances to step S354. For example, if an event, including a sound-production request, of insufficiency of the residual amount of the battery of the internal power source 211 occurs, an interrupt caused by the sound-production request is generated, and the process advances to step S354. Note that events to be notified include an event which occurs in accordance with the operation sequence of the X-ray imaging apparatus 101 and an event which occurs at an arbitrary timing during the operation of the X-ray imaging apparatus 101. Examples of the event which occurs at an arbitrary timing are detection of insufficiency of the residual amount of the battery and detection of disconnection of communication with the external apparatus. In step S354, the control unit 204 determines whether the interrupt has been caused by the sound-production request to request execution of sound production. If the interrupt has been caused by the sound-production request, the process advances to step S355, and the control unit 204 drives the notification unit 208 to execute sound production in accordance with the sound-production request. In this way, the control unit 204 causes the sound-production unit to execute sound production in response to detection of an event as the source of the sound-production request.

The interrupt processing executed in response to an interrupt signal associated with sound production has been explained. As is well known, the interrupt processing is immediately executed in response to generation of an interrupt signal after an interrupt is allowed in step S301. Therefore, the sound-production settings are updated, as needed, in accordance with a sound-production setting operation, and the loudspeaker of the notification unit 208 produces a sound in response to the occurrence of an event associated with sound production, such as a decrease in battery voltage.

Referring back to FIG. 3A, after allowing an interrupt of the sound-production request in step S301, the control unit 204 determines in step S302 whether an imaging operation request has been issued. An imaging request is issued based on an imaging sequence start instruction from the imaging console 102 or the like. If it is determined in step S302 that the imaging request has been issued, the process advances to step S303. In steps S303 to S307, X-ray imaging is executed.

In step S303, the control unit 204 performs imaging preparation for X-ray imaging. After completion of the imaging preparation, the control unit 204 starts, in step S304, X-ray imaging in response to an irradiation start request from the X-ray generation console 107, and waits for the end of X-ray imaging (completion of X-ray irradiation). During imaging, charges are accumulated in the respective pixels of the sensor array 251 by emitted X-rays. Upon completion of X-ray irradiation, the control unit 204 starts reading out signals from the sensor array 251 by the reading unit 203 in step S305. When reading out the image signals, the reading unit 203 reads out image signals from the detector array of the sensor unit 201, digitalizes the image signals, and stores the digital signals as X-ray image data in the storage unit 205. Upon completion of the operation of reading out the image signals from the detector array, the process advances from step S306 to step S307. In step S307, the control unit 204 transfers the X-ray image stored in the storage unit 205 to the imaging console 102 using the communication unit 206.

Note that in the above example, the interrupt processing (FIG. 3B) is immediately executed in response to a setting request or a sound-production request. However, the timing at which the interrupt processing is executed is not limited to this. For example, a method of holding a setting request or a sound-production request as a flag and confirming the flag for every predetermined time or the like may be adopted.

During a readout period started in step S305 described above, the digital image is read out from the detector array of the sensor unit 201. More specifically, this operation is executed as follows. First, the sensor driving unit 202 selects a row of the detector array of the sensor unit 201, and the reading unit 203 samples and holds charges accumulated in respective pixels connected to the selected row. The reading unit 203 A/D-converts the sampled and held charges to perform digitalization. The operation of reading out signals from the respective pixels of the selected row in this way is called a fast scan. Next, the sensor driving unit 202 selects a row different from the last selected row in the sensor unit 201, and executes the above-described fast scan. This operation is performed for rows corresponding to a preset readout area. The operation of switching the selected row is called a slow scan. A desired digital image is obtained by the fast scan and slow scan.

Note that to create one image, some X-ray imaging apparatuses 101 acquire two images in total, that is, an offset information image of the detector array and an image after X-ray irradiation. In this case, there are readout periods for acquiring the respective images. Note that the offset information image is, for example, a dark image acquired from the detector array without performing X-ray irradiation.

The above-described readout period is a period during which a very small amount of charges necessary for image generation is extracted. If sound production of the loudspeaker overlaps this period, electromagnetic noise generated by the sound-production operation of the loudspeaker may generate an induced electromotive force on the sensor array and a current by the induced electromotive force, thereby generating image noise. FIGS. 4A, 4B, 5A, 5B, 6A, and 6B are views schematically showing the principle when the sound-production operation of the loudspeaker generates noise in an image.

For the sake of simplicity, when a sound produced from the loudspeaker is represented by a sinusoidal wave Wa and its frequency is represented by fa (unit: Hz), a period Ta (unit: sec) is given by Ta=1/fa. As described above, a sample and hold operation and A/D conversion are performed for each row. Thus, a period for selecting a readout row is equal to a sampling period. When the sampling period is represented by Ts (unit: sec) and a sampling frequency is represented by fs (unit: Hz), Ts=1/fs holds.

Figure 4A:
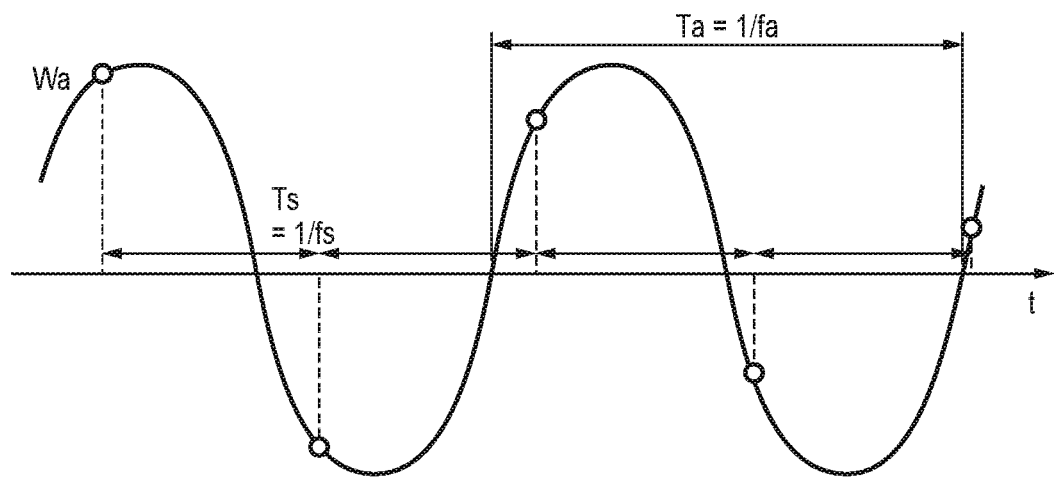
FIGS. 4A and 4B are views for explaining the principle of image noise generation by a sound-production operation.
Figure 4B:
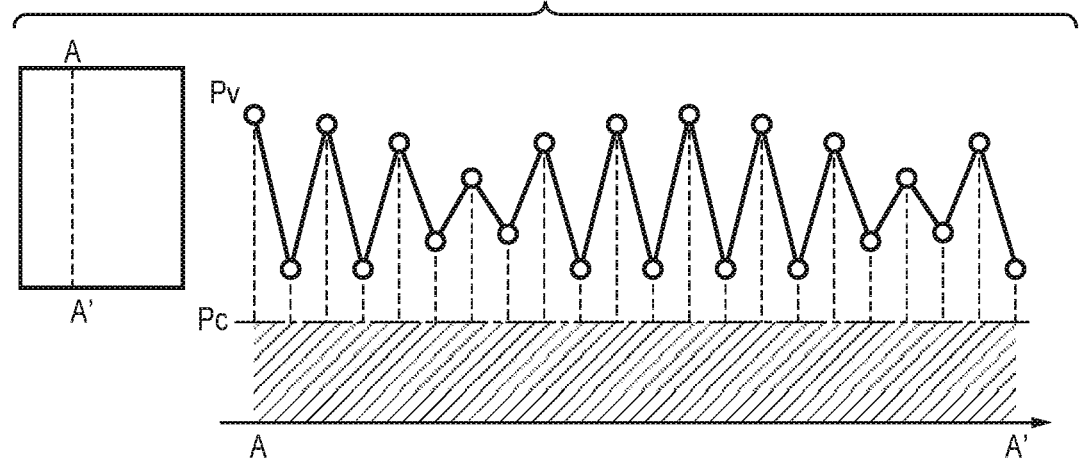

FIG. 4A shows sampling of an electromagnetic noise component (to be referred to as a noise component caused by sound production hereinafter) generated by the sound-production operation of the loudspeaker when fs≥2×fa (or Ts≤Ta/2) is satisfied, that is, when the sampling theorem is satisfied. In an actual operation, a charge component (in other words, an image component) corresponding to an X-ray incident dose is sampled at the same time, and the noise component caused by sound production is superimposed on the charge component. For the sake of descriptive simplicity, however, FIG. 4A shows only the noise component caused by sound production. Since the sampling theorem is satisfied, the frequency component of the sound-production frequency fa is reflected on a sampling result. FIG. 4B is a sectional view taken along a line A-A' in the slow-scanning direction of the acquired image signals. For the sake of simplicity, when an actual image component corresponding to the X-ray incident dose has a uniform value Pc, a pixel value Pv is obtained by superimposing the noise component caused by sound production on the value Pc of the image component. Since the component of the sound-production frequency fa is reflected on the sampling result, periodic noise of the frequency fa appears in the image. The sampling period Ts on the time axis is extracted as an adjacent row in the image. For example, a periodic component extracted at a period of n rows in the image is that having a period of Ts×n (unit: sec) on the time axis. In the case of FIGS. 4A and 4B, therefore, noise having, as a period, the number of rows represented by Ta/Ts is superimposed on the image.

Figure 5A:
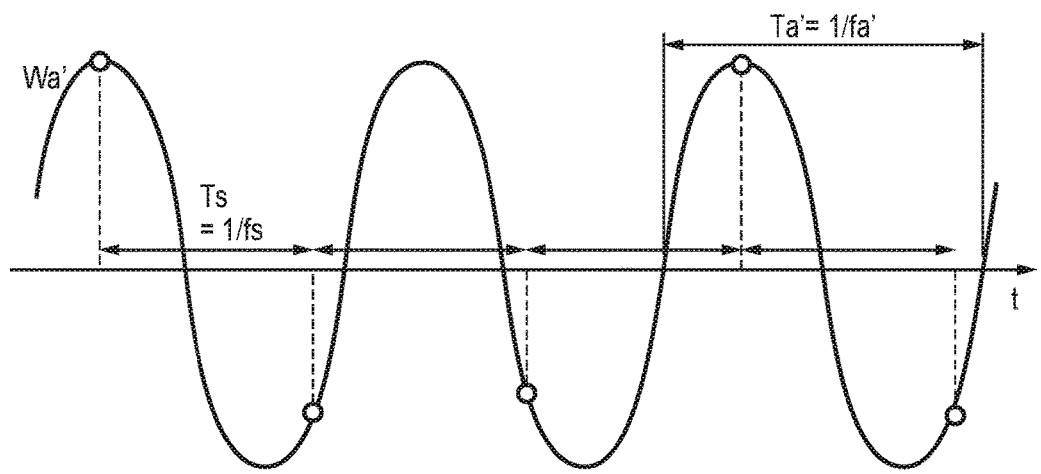
FIGS. 5A and 5B are views for explaining the principle of image noise generation by a sound-production operation.
Figure 5B:
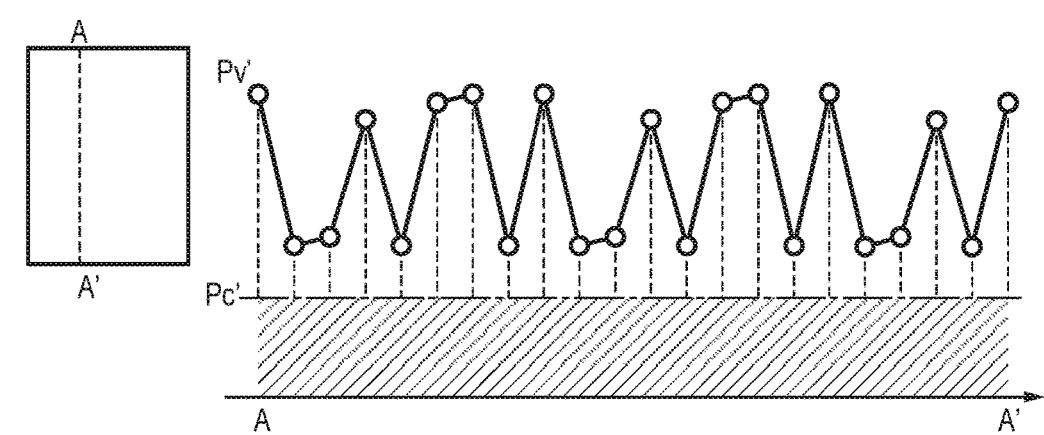
Figure 6A:
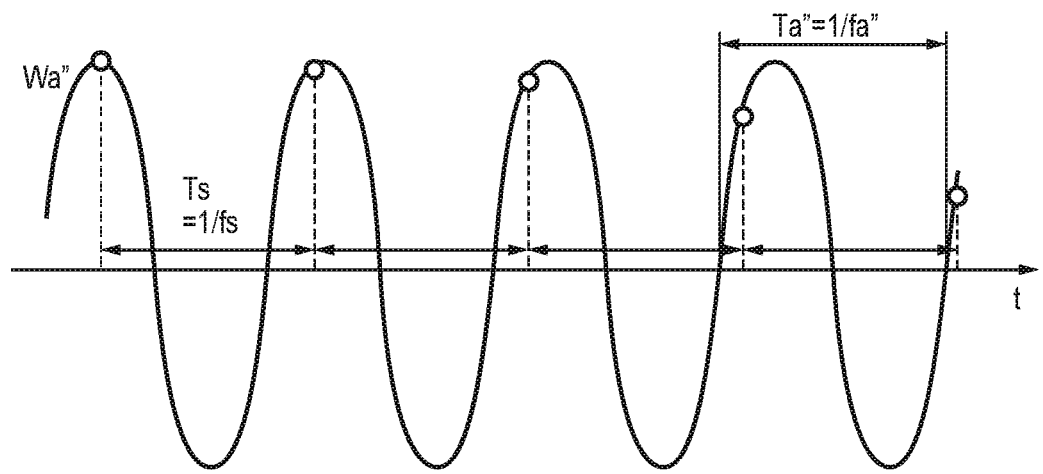
FIGS. 6A and 6B are views for explaining the principle of image noise generation by a sound-production operation.
Figure 6B:
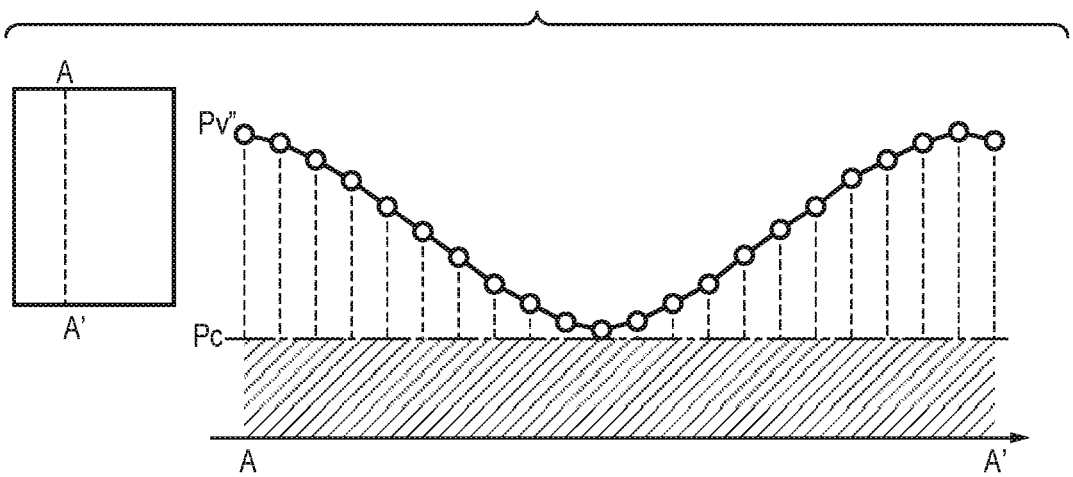

FIG. 5A shows sampling of an electromagnetic noise component generated by the sound-production operation of the loudspeaker when fs<2×fa' (or Ts>Ta'/2) is satisfied, that is, when the sampling theorem is not satisfied. FIG. 5B is a sectional view taken along the line A-A' in the slow-scanning direction of the image signals on which the electromagnetic noise component shown in FIG. 5A is superimposed. Since the sampling theorem is not satisfied, the frequency component of the sound-production frequency fa are not reflected on the sampling result, and periodic noise (noise caused by aliasing (to be described later)) is generated on the lower-frequency side with respect to the sampling frequency and the sound-production frequency. FIGS. 6A and 6B show a case in which the ratio of a row sampling frequency to the sound-production frequency is further lowered to almost equalize the frequencies. Similarly to FIGS. 5A and 5B, the sampling theorem is not satisfied. The frequency of periodic noise (noise caused by aliasing (to be described later)) to be superimposed on the image is very low.

Figure 7A:
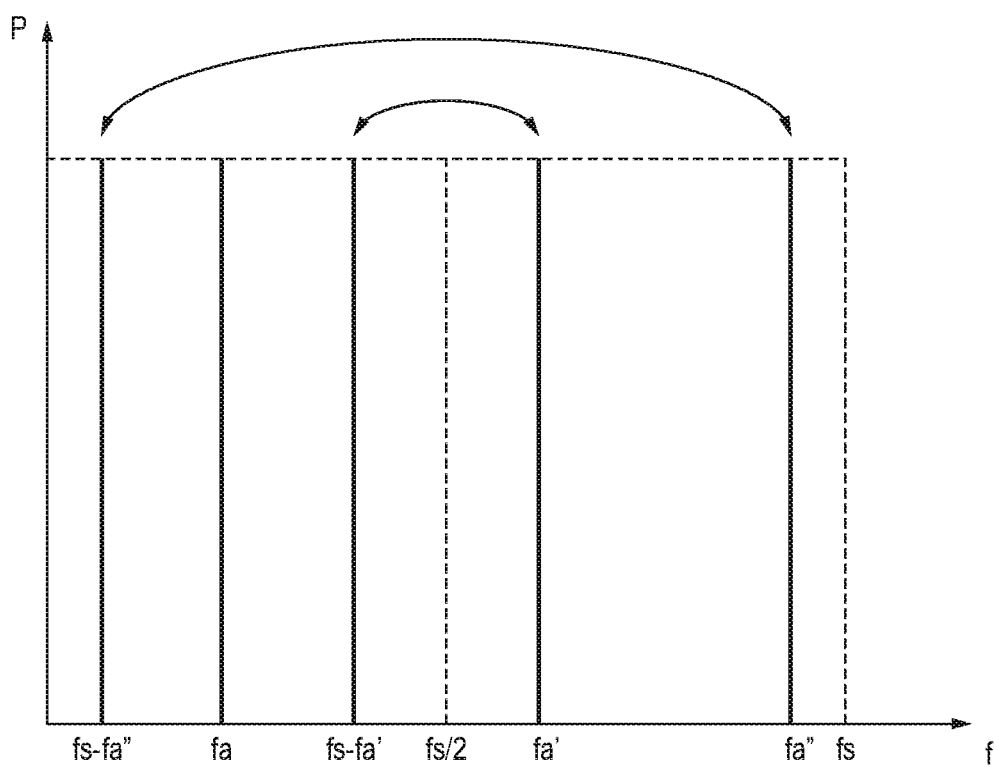
FIGS. 7A and 7B are views for explaining the sampling theorem.
Figure 7B:
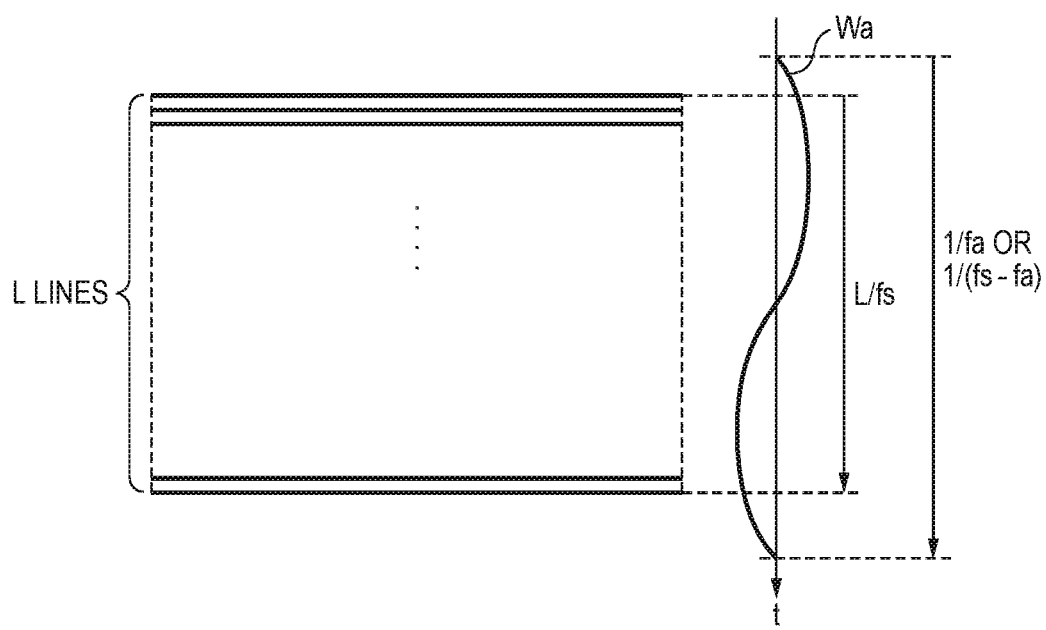

This phenomenon is caused by aliasing which occurs when the sampling theorem is not satisfied. FIGS. 7A and 7B are views showing power spectra for explaining the phenomenon. If the sampling theorem is satisfied in FIGS. 4A and 4B, the frequency component of noise caused by sound production is held even after sampling, and thus appears at fa on the frequency axis. If sound production exceeding the Nyquist frequency fs/2 is performed in FIGS. 5A, 5B, 6A, and 6B, noise caused by sound production is generated at frequencies (fs−fa' in the case of FIGS. 5A and 5B and fs−fa" in the case of FIGS. 6A and 6B) obtained by folding at the Nyquist frequency. In the case of FIGS. 5A and 5B, since sound production is performed at a frequency close to the Nyquist frequency, folding noise is generated at a high frequency close to the Nyquist frequency. To the contrary, in the case of FIGS. 6A and 6B, although sound production itself is performed at a frequency higher than that in FIGS. 5A and 5B, the frequency of folding noise which influences the image is lower than that in FIGS. 5A and 5B (fs−fa'>fs−fa").

No noise is ideally generated in a medical image. However, there is no problem even if noise exists within a range in which diagnosis is not influenced or a range in which a human cannot identify noise. For example, in a conventional imaging method using an X-ray film, X-ray irradiation error (shading) caused by the geometrical shape of the focal point of the X-ray tube is superimposed on an image on the X-ray film but such image can be used for diagnosis. From this viewpoint, it can be considered that noise of a very low frequency hardly influences diagnosis. For example, if periodic noise exists for a period longer than one period in one image, there exist a plurality of shaded portions on the image, and thus it becomes easy to recognize noise. To the contrary, in an image in which periodic noise exists for a period shorter than one period, an observer cannot recognize noise or no influence is exerted on diagnosis even if shades can be recognized, similarly to shading of the X-ray tube. In this example, noise exists for a period shorter than one period in one image. However, when observing an observation area partially extracted from an image, the same effect can be obtained as long as noise exists for a period shorter than one period in the extracted observation area.

As a sound produced from the notification unit 208, a sound having a fundamental frequency which satisfies a condition determined based on the number of rows of the image read out from the sensor unit 201 and the readout frequency of the signals of each row is used. That is, L (L≥2) represents the number of rows of a predetermined area (the whole or predetermined part (observation area) of the image read out from the sensor unit 201) of one image, and fs represents the readout frequency (to be referred to as a row readout frequency hereinafter) of the signals of each row.

In this case, it is possible to avoid the influence of noise caused by sound production on diagnosis by setting the fundamental frequency fa of a sound to be produced, as follows.

$$fa \leq fs/L \text{ for } fa \leq fs/2 \quad (1)$$

$$fa \geq (L-1)fs/L \text{ for } fa > fs/2 \quad (2)$$

The above cases will be described below with reference to FIG. 7B.

For fa≤fs/2, the frequency of noise generated in a medical image by sound production of the frequency fa is fa, as described with reference to FIG. 7A. As shown in FIG. 7B, to avoid the influence of noise caused by sound production on diagnosis, the noise caused by sound production needs to exist for one period or shorter in one image. To achieve this, the readout period (L×Ts=L/fs) of one image (an image of L rows) needs to be one period (Ta=1/fa) or shorter of the noise caused by sound production. Therefore, fa is selected to satisfy 1/fa≥L/fs, that is, inequality (1).

Furthermore, for fa>fs/2, noise generated in a medical image by sound production of the frequency fa is noise caused by aliasing, and the frequency of the noise is represented by fs−fa, as described with reference to FIG. 7A. Similarly to the above case, to make noise exist for one period or shorter in one image, the readout period (L/fs) of one image (L rows) need only be one period (1/(fs−fa)) or shorter of folding noise (aliasing). That is, 1/(fs−fa)≥L/fs need only be satisfied. By solving this inequality for fa, inequality (2) is obtained. Then, fa is selected to satisfy inequality (2).

The above-described restriction on the frequency of sound production is applied to, for example, the fundamental frequency of a sound. As for a sound having the fundamental frequency fa, various harmonic waves such as harmonic tones are superimposed. Therefore, for example, even if the fundamental frequency fa is limited in accordance with inequality (1), the superimposed harmonic wave may not satisfy inequality (1) above. However, a harmonic component is generally smaller than a fundamental frequency component, and thus the image suffers a small influence. Furthermore, if the frequency of the harmonic wave satisfies inequality (2), the influence on the image is negligible.

Note that the condition indicated by inequalities (1) and (2) is synonymous with disuse of a sound having, as a fundamental frequency, the frequency f satisfying fs/L<f< (L−1) fs/L.

The operation of the X-ray imaging system 100 in the synchronization mode in which the X-ray imaging apparatus 101 executes X-ray imaging in cooperation with the X-ray generating apparatus 108 will be described with reference to a flowchart shown in FIG. 8. FIG. 8 is a flowchart illustrating exchange between the imaging console 102, the X-ray imaging apparatus 101, and the X-ray generating apparatus 108 at the time of imaging according to this embodiment. Note that the X-ray generating apparatus 108 and the X-ray imaging apparatus 101 are connected via the connection device 109, as shown in FIG. 1, and are configured to exchange data concerning irradiation allowance. The imaging console 102 and the X-ray imaging apparatus 101 are connected via the LAN 103, as shown in FIG. 1.

To start imaging, the respective apparatuses are activated in steps SC401, SD401, and SX401. In step SC402, the imaging console 102 accepts designation of the X-ray imaging apparatus 101 to be used, and input of imaging information such as an imaging target person and an imaging portion. If the X-ray imaging apparatus 101 to be used is preset at the time of last activation or the like, and it is not necessary to change the setting, designation of the X-ray imaging apparatus can be omitted in some cases. In step SX402, the X-ray generating apparatus 108 accepts irradiation conditions such as the irradiation time and intensity of X-rays input via the X-ray generation console 107.

In addition to the above settings concerning the irradiation conditions and imaging information, the user can make sound-production settings as settings concerning a notification made by the X-ray imaging apparatus 101. Steps SC403 and SD403 indicate that the operation input of the sound-production settings can be accepted. Practical contents of the sound-production settings include the volume of the sound produced from the notification unit 208 (sound-production unit) of the X-ray imaging apparatus 101, an ON/OFF setting indicating whether to produce a sound, and correspondences between types of sounds and events to be notified, as described above. The sound-production settings can be made from one or both of the imaging console 102 and the operation unit 207 of the X-ray imaging apparatus 101 (steps SC403 and SD403). Note that in setting of correspondences between sounds and events to be notified, a specific event (detection of insufficiency of the residual amount of the battery, detection of disconnection of communication with the external apparatus, or the like) occurring at an arbitrary timing is prohibited from being associated with a sound which does not satisfy the above-described limitation of the fundamental frequency.

If sound settings are made from the imaging console 102, the imaging console 102 may be configured to make, after setting information of the X-ray imaging apparatus 101 to be used, sound-production settings in the X-ray imaging apparatus 101. Contents of the sound-production settings instructed by the imaging console 102 are sent to the X-ray imaging apparatus 101, and the X-ray imaging apparatus 101 updates the sound-production settings. This is represented by steps SC403 and SD404. If sound settings are made using the operation unit 207 of the X-ray imaging apparatus 101, it is only necessary to change the volume or set whether to output a sound, in accordance with an operation of the switch, the dial, or the like provided in the operation unit 207.

These sound-production settings can be made all the time in principle. However, in consideration of the user's intention to confirm the volume after actually making settings, the sound-production settings can be preferably made while the X-ray imaging apparatus 101 is active. Since it is preferable to be able to confirm a sound immediately after the setting operation by the user, at least a timing before the X-ray imaging apparatus 101 can accept X-ray irradiation to generate an image is preferable. By exemplifying FIG. 8, at a timing before the X-ray imaging apparatus 101 executes step SD405 (imaging preparation start), sound-production settings can be accepted.

When the respective apparatuses of the X-ray imaging system 100 are activated and an imaging sequence can start, an instruction (step SC404) of "imaging sequence start" from the imaging console 102 causes the X-ray imaging apparatus 101 to enter the imaging sequence (step SD405). In this example, the start instruction (imaging sequence start) from the imaging console 102 is used as a trigger. However, after the respective apparatuses are activated, the X-ray imaging apparatus 101 may transit to an imaging enable state.

Upon receiving an imaging sequence start notification from the imaging console 102, the X-ray imaging apparatus 101 starts preparation in step SD405 so that X-ray irradiation can be performed. More specifically, processing of, for example, supplying a current to the sensor unit 201 and waiting until the operation of a corresponding portion (for example, the sensor array 251) becomes stable is performed. Upon completion of the imaging preparation, the X-ray imaging apparatus 101 can respond to an irradiation request from the X-ray generating apparatus 108, the X-ray generation console 107, or the like. If the X-ray generating apparatus 108 outputs an irradiation start request at a timing (before completion of the imaging preparation) at which the X-ray imaging apparatus 101 cannot allow irradiation (step SX403), the X-ray imaging apparatus 101 outputs an irradiation NG signal or does not respond continuously. If the irradiation NG signal is returned or a non-response state is maintained, the X-ray generating apparatus 108 starts no X-ray irradiation.

Upon completion of the imaging preparation, the X-ray imaging apparatus 101 notifies the user of an irradiation enable state using the notification unit 208 in step SD406. In the notification from the notification unit 208, a notification by light and a notification by a sound are made at the same time. As for a notification by a sound, sound production may be executed only once at the time of completion of the preparation, or a sound may be continuously produced until X-ray irradiation is actually executed. The length of the sound may be changed by the above-described sound-production settings instead of a fixed length. Furthermore, the X-ray imaging apparatus 101 may notify the imaging console 102 of completion of the imaging preparation, and the imaging console 102 may notify the user of completion of the imaging preparation using the display unit.

If the X-ray generating apparatus 108 outputs the irradiation start request, as indicated by step SX404, after the X-ray imaging apparatus 101 enters a state in which it can deal with an irradiation request, the X-ray imaging apparatus 101 returns an irradiation allowance notification to the X-ray generating apparatus 108 in step SD408. The X-ray imaging apparatus 101 causes the sensor array 251 to shift to a state in which charges of an X-ray-charge conversion result are accumulated. Upon receiving the irradiation allowance notification from the X-ray imaging apparatus 101, the X-ray generating apparatus 108 starts X-ray irradiation from the X-ray tube 106 in step SX405. After that, upon completion of X-ray irradiation, the X-ray generating apparatus 108 notifies the X-ray imaging apparatus 101 of it in step SX406.

If the X-ray imaging apparatus 101 receives the irradiation completion notification from the X-ray generating apparatus 108 or a predetermined irradiation time elapses, the X-ray imaging apparatus 101 starts reading out accumulated charges from the detector array in step SD410. As described above, the X-ray imaging apparatus 101 drives the sensor driving unit 202 and the reading unit 203 to read out the charges (signals) from the detector array. The X-ray imaging apparatus 101 digitalizes the charges (signals). And the X-ray imaging apparatus 101 saves the digital signals as image data in the storage unit 205.

Examples of the notification contents of the sound-production request which can be generated independently of the imaging sequence are a warning of the residual amount of the battery at the time of battery driving and disconnection of wireless communication when wireless communication is used for communication between the imaging console 102 and the X-ray imaging apparatus 101. For example, if the X-ray imaging apparatus 101 is driven by the battery, the residual amount of the battery decreases along with the use time, and the function stops eventually. Therefore, to prevent the function from suddenly stopping, when the residual amount of the battery becomes equal to or smaller than a predetermined amount, the user is notified of it. Therefore, a notification (sound production) of a decrease in residual amount of the battery may coincide with the image readout operation from the detector array. If sound production coincides with the image readout operation from the detector array, driving of the loudspeaker influences the image readout operation. In the above embodiment, the influence on the image readout operation is reduced by setting the fundamental frequency of a sound to be produced, as described above.

Referring to FIG. 8, when the image readout operation in step SD410 ends, the X-ray imaging apparatus 101 transfers, in step SD411, the image data stored in the storage unit 205 to the imaging console 102. In step SC405, the imaging console 102 receives the image data sent from the X-ray imaging apparatus 101. In step SC406, the imaging console 102 saves the received image data in a connected storage device (not shown), and displays it on the display unit.

As described above, according to the first embodiment, it is possible to suppress the influence of sound production on an image to be read out, even if a sound-production component produces a sound during the readout period associated with image generation. That is, in the X-ray imaging apparatus according to the first embodiment, a sound produced from the notification unit 208 has a fundamental frequency based on the readout frequency of signals in the sensor unit 201. For example, a sound having the fundamental frequency fa which satisfies the condition indicated by inequality (1) or (2) above is used. This suppresses the influence of noise caused by sound production in the image.

Second Embodiment

The first embodiment has explained the arrangement for reducing the influence of noise caused by sound production at the time of reading out signals from the sensor unit 201 (detector arrays) in the X-ray imaging apparatus 101 operating in the synchronization mode. The second embodiment will describe an example of an X-ray imaging apparatus 101 operating in an X-ray irradiation detection mode.

The X-ray irradiation detection mode and an X-ray irradiation detection function will be described first. The X-ray irradiation detection function is a function of determining the presence/absence of X-ray irradiation by the X-ray imaging apparatus 101 and starting, if it is determined that X-ray irradiation is being performed, X-ray imaging. If X-ray imaging starts, a sensor unit 201 accumulates charges by X-rays, and the charges are read out as an X-ray image from the sensor unit 201. The X-ray irradiation detection mode is a mode of acquiring an X-ray image by the above-described X-ray irradiation detection function. Thus, in the X-ray irradiation detection mode, it is unnecessary to exchange notifications concerning X-ray irradiation between an X-ray generating apparatus 108 and the X-ray imaging apparatus 101 in an X-ray imaging system 100 (FIG. 1), and the connection device 109 and the like can be eliminated.

FIG. 9 shows an example of the arrangement of the X-ray imaging apparatus 101 having the X-ray irradiation detection function. This arrangement is obtained by adding an X-ray irradiation detecting unit 501 to the arrangement (FIG. 2) of the X-ray imaging apparatus 101 described in the first embodiment. The X-ray irradiation detecting unit 501 detects radiation irradiation to the sensor unit 201 by sampling a current value flowing through a bias wiring connected to a plurality of radiation detecting elements of the sensor unit 201. There are various implementation methods of the X-ray irradiation detecting unit 501, such as a method of detecting radiation irradiation using the same scintillator and photosensor as those of the sensor unit 201, and a method of detecting a current generated in the sensor unit 201 by X-ray irradiation, which will be described in this embodiment. Any known method may be used for the X-ray irradiation detecting unit 501. Note that the X-ray irradiation detecting unit 501 according to this embodiment will be described with reference to FIGS. 10 and 11 (a bias current measurement unit 1028 and an A/D converter 1029).

Figure 10:
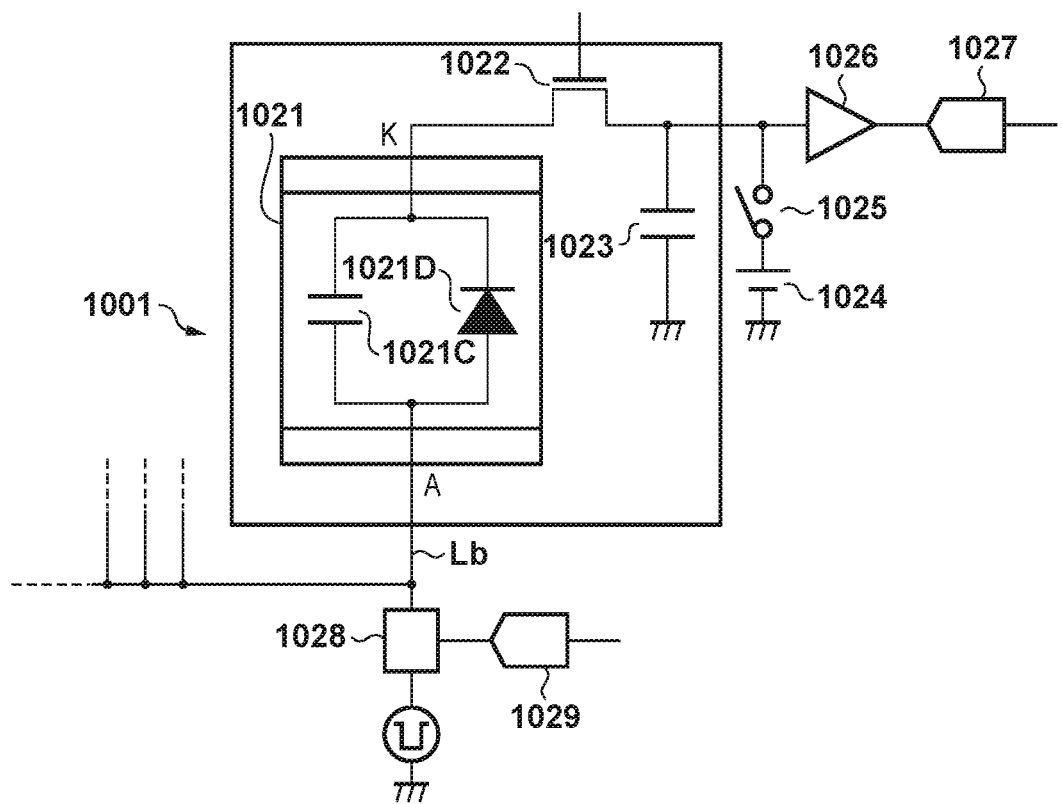
FIG. 10 is a circuit diagram showing the circuit arrangement of a detector.

An X-ray irradiation detection method according to the second embodiment will be described next. FIG. 10 shows the equivalent circuit of a detector forming one pixel of the sensor unit 201. One element includes a photoelectric conversion element 1021 and a switching TFT 1022 for controlling charge accumulation and readout. The photoelectric conversion element 1021 is used to convert, into an electrical signal, visible light generated in accordance with the dose of X-rays with which a scintillator (not shown) is irradiated, and functions as a radiation detecting element in cooperation with the scintillator. Note that instead of the photoelectric conversion element, an element for directly converting emitted X-rays into an electrical signal may be used (in this case, the scintillator becomes unnecessary). A capacitor 1021C in the photoelectric conversion element 1021 may be a parasitic capacitance of a photodiode 1021D or a capacitor intentionally added to improve the dynamic range of the detector. An anode A of the photodiode 1021D is connected to a bias wiring Lb as a common electrode. A cathode K is connected to the switching TFT 1022 for reading out charges accumulated in the capacitor 1021C. By performing irradiation of X-rays 1001 after the capacitor 1021C is reset by operating the switching TFT 1022 and a reset switching element 1025, charges corresponding to the dose of emitted X-rays are generated in the photodiode 1021D and accumulated in the capacitor 1021C. After that, by operating the switching TFT 1022 again, a signal charge is transferred to a capacitor 1023. An amplifier 1026 then reads out, as a potential signal, the amount of charges accumulated in the photodiode 1021D. An A/D converter 1027 A/D-converts the potential signal. The A/D converter 1027 outputs the converted signal as an incident X-ray dose.

Figure 11:
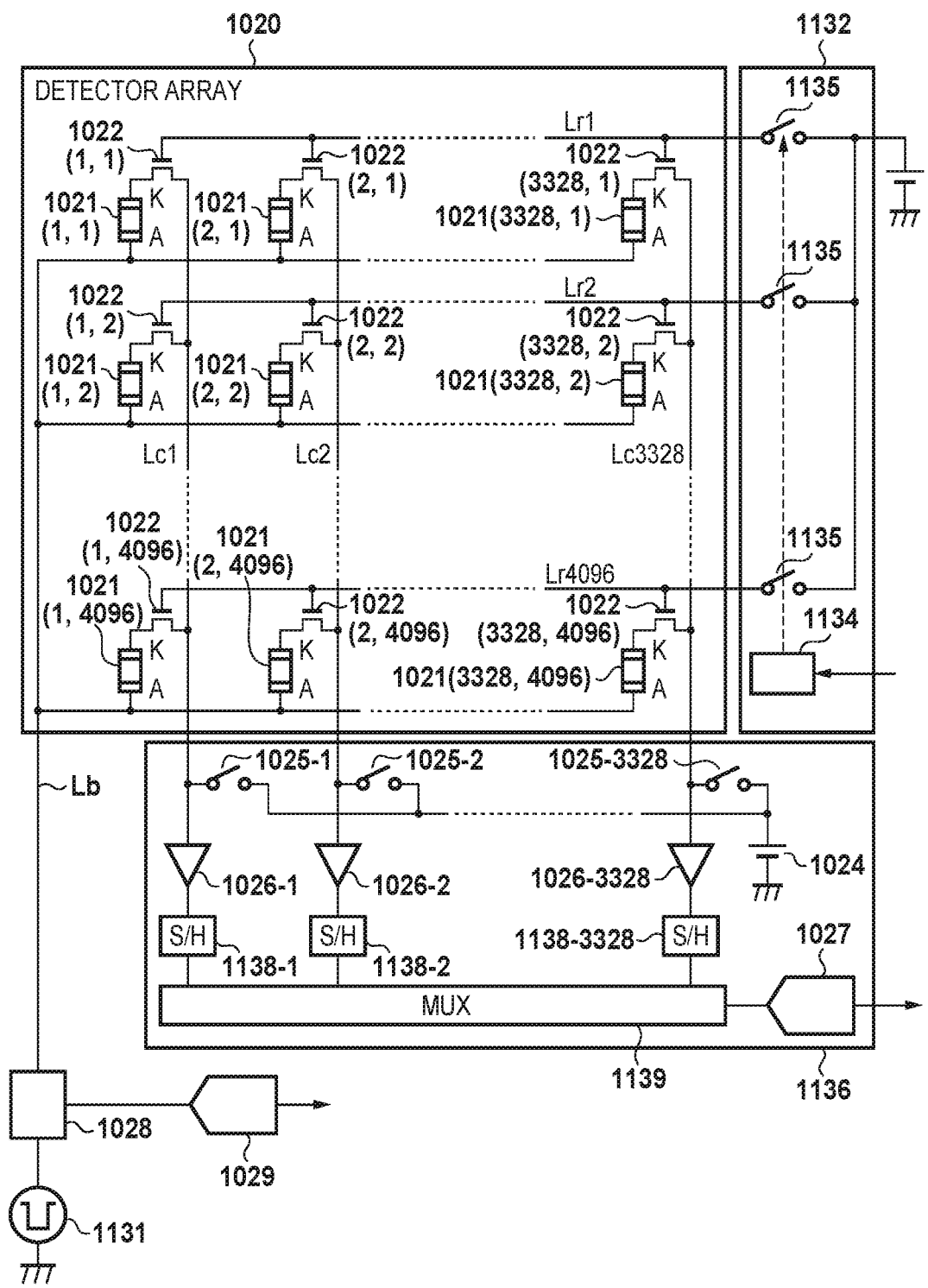
FIG. 11 is a circuit diagram showing the circuit arrangement of a detector array.

FIG. 11 shows the equivalent circuit of the detector array forming the sensor unit 201. In this example, the detector array is formed from 3328×4096 pixels. As shown in FIG. 10, each pixel includes the photoelectric conversion element 1021 and the switching TFT 1022. The K electrode of a photoelectric conversion element 1021 (m, n) on each column of the detector array is connected to a corresponding one of common column signal lines Lc1 to Lc3328 corresponding to the respective columns via the source/drain conductive path of a corresponding switching TFT 1022 (m, n). The A electrodes of the photoelectric conversion elements 1021 on each row are connected to a bias power source 1131 via the common bias wiring Lb.

The gate electrodes of the switching TFTs 1022 on respective rows are connected to row selection lines Lr1 to Lr4096. Each row selection line Lr is connected to a sensor driving unit 202 via a row selection unit 1132. The row selection unit 1132 includes, for example, an address decoder 1134 and 4,096 switch elements 1135. This arrangement makes it possible to read out signals from pixels on an arbitrary row Lrn.

Each column signal line Lc is connected to a signal readout unit 1136 controlled by a reading unit 203. The signal readout unit 1136 includes the reset switching elements 1025 for resetting the column signal lines Lc to the potential of a reset reference power source 1024, the amplifiers 1026, sample/hold circuits 1138, an analog multiplexer 1139, and the A/D converter 1027. The detector array according to this embodiment includes 3328×4096 pixels, and the outputs of 3328 pixels for one column are simultaneously read out to the column signal lines Lc1 to Lc3328. The signals (analog signals) read out to the column signal lines Lc are sequentially output to the A/D converter 1027 by the analog multiplexer 1139 via the amplifiers 1026-1 to 1026-3328 and the sample/hold circuits 1138-1 to 1138-3328. The signals are output as digital data.

All the switching TFTs 1022 are turned off during an accumulation operation. In this state, signal charges are accumulated in the photoelectric conversion elements 1021. An operation of reading out the accumulated signal charges causes the address decoder 1134 to sequentially turn on the switch elements 1135 to drive the switching TFTs 1022 connected to the row selection lines Lr1 to Lr4096 row by row. The signal charges accumulated in the capacitors 1021C are read out to the column signal lines Lc1 to Lc3328 when the switching TFTs 1022 are ON.

The photoelectric conversion element 1021 generates dark charges even in a period during which no X-ray irradiation is performed. The dark charges are accumulated in the capacitor 1021C as in the case during the accumulation operation. These accumulated charges correspond to dark noise which cannot be formed into an X-ray image, and are accumulated in the capacitor 1021C with the lapse of time, thereby exerting an influence such as a reduction in dynamic range at the time of X-ray imaging. It is therefore necessary to perform idle readout operation to remove the influence (dark noise). Since the idle readout operation reads out charges accumulated in the capacitors 1021C, similarly to a normal readout operation, the operation of the detector array is the same as the readout operation. That is, the address decoder 1134 sequentially turns on the switch elements 1135 to drive the switching TFTs 1022 row by row, thereby reading out the charges accumulated in the capacitors 1021C to the column signal lines Lc1 to Lc3328. Since idle readout operation is performed to sweep dark noise components, the readout charges are unnecessary as data. Hence, unlike the normal readout operation, it is not necessary to operate the sample/hold circuit 1138, the analog multiplexer 1139, and the A/D converter 1027 after the amplifier 1026.

Although the charges generated in the photodiode 1021D by X-ray irradiation are accumulated in the capacitor 1021C, the charges partially leak to the bias wiring Lb to generate current fluctuations corresponding to the dose of X-rays in the bias wiring Lb. By observing this current value, it is possible to grasp an X-ray irradiation state. The current fluctuations are converted into voltage values by the bias current measurement unit 1028. The current fluctuations are converted into digital values by the A/D converter 1029. The output values correspond to the dose of X-rays entering the photoelectric conversion element 1021. The apparatus waits until X-ray irradiation starts by operating the bias current measurement unit 1028 and the A/D converter 1029 while sweeping the dark noise components by the idle readout operation. When the output of the A/D converter 1029 exceeds a preset threshold, a control unit 204 determines detection of X-ray irradiation. If detection of X-ray irradiation is determined, the control unit 204 shifts the operation mode of the detector array from the idle readout operation to the accumulation operation. In the accumulation operation, each of the photoelectric conversion elements 1021 of the detector array accumulates charges corresponding to X-ray irradiation. The control unit 204 acquires X-ray image data by shifting the operation mode of the detector array to the readout mode after performing the accumulation operation until X-ray irradiation ends.

As described above, since X-ray irradiation detection includes a periodic sampling operation, the influence of electromagnetic noise generated by a sound-production operation is exerted, similarly to the first embodiment. In X-ray irradiation detection, a small variation in leak current to the bias wiring Lb is detected, and thus X-ray irradiation detection tends to be influenced by an external factor. Therefore, noise caused by sound production is sampled. If the magnitude of the noise exceeds the above threshold, it may be erroneously determined that X-ray irradiation has been performed although no X-ray irradiation has actually been performed. To reduce such influence, for example, correlated double sampling can be used as processing of reducing periodic noise. Correlated double sampling is processing of sampling a signal at the same point twice at a predetermined time interval, and outputting, as a signal, the difference between the sampled signals.

A current flowing through the bias wiring Lb by X-ray irradiation detection is sampled at the timing when the switching TFTs 1022 are turned on at the time of the idle readout operation, and the difference between the sampled current and data sampled at the timing when the switching TFTs 1022 are turned off immediately before/after the switching TFTs 1022 are turned on is acquired. The sampling time when the switching TFTs 1022 are ON is represented by t, and preceding and succeeding sampling times when the switching TFTs are OFF are respectively represented by "t−Δt" and "t+Δt". In addition, a bias current at time x is represented by I(x), a current flowing through the switching TFTs 1022 at time x is represented by Ion(x), and the reference voltage of an amplifier (not shown) in the bias current measurement unit 1028 is represented by V. In this case, as a function of the sampling time, an output D of the A/D converter 1029 is given by:

$$D(t-\Delta t)=G\{RI(t-\Delta t)+V(t-\Delta t)\} \quad (3)$$

$$D(t)=G\{RI(t)+V(t)+RIon(t)\} \quad (4)$$

$$D(t+\Delta t)=G\{RI(t+\Delta t)+V(t+\Delta t)\} \quad (5)$$

where G represents the gain of the amplifier (not shown) in the bias current measurement unit 1028, and R represents the resistance component of a wiring connected to the bias current measurement unit.

In correlated double sampling according to this embodiment, the current value sampled at the time (at time t) of execution of the readout operation of signals for each row from the sensor unit 201, and the average value of the two current values sampled before and after (t±Δt) the readout operation are used. That is, it is possible to obtain a result of correlated double sampling given by:

$$D(t)-\{D(t-\Delta t)+D(t+\Delta t)\}/2 \approx GRIon(t) \quad (6)$$

It will be understood that noise V(t) superimposed on the reference voltage and noise RI(t) superimposed on the bias wiring Lb are removed, and only components by a bias current when the switching TFTs are ON are extracted. Note that in correlated double sampling, one of the current values sampled before and after (t+Δt and t−Δt) readout of the row by the idle readout operation may be used instead of the above-described average value.

When performing the idle readout operation while switching the rows one by one, the bias current when the TFTs are OFF is sampled from when the bias current when the TFTs are ON is sampled until the idle readout operation for the next row is performed. Thus, the sampling period is Ts/2 with respect to the idle readout period Ts. Since an idle readout frequency at this time is fs=1/Ts, the sampling frequency is 2×fs. In the above-described correlated double sampling, one data is formed from three sampling results. Consequently, at the above-described sampling frequency, the effect of reducing periodic noise within a frequency range in which the sampling theorem is satisfied is produced. Therefore, the condition that the fundamental frequency fa of periodic noise, in this example, a sound to be produced is ½ or less of the frequency of sampling of the current value performed by the X-ray irradiation detecting unit 501 is satisfied. That is, it is possible to suppress the influence of noise caused by sound production within a range in which $$fa \leq (2 \times fs)/2 = fs \quad (7)$$

is satisfied.

If an X-ray output band is from fl to fh, a bandpass filter which passes this frequency band can be provided in the bias current measurement unit 1028, thereby reducing the influence of noise in other frequency bands. In this example, if no correlated double sampling is applied, the sampling frequency of the bias current is set to fs. Then, it is possible to suppress the influence of noise caused by sound production by separating the X-ray output from a noise component caused by sound production, by setting fa and fs to satisfy a condition given by:

$$fa < fl \text{ or } fa > fh \text{ for } fa \leq fs/2 \quad (8)$$

$$fs-fa < fl \text{ or } fs-fa > fh \text{ for } fa > fs/2 \quad (9)$$

If the X-ray irradiation detecting unit 501 detects that X-ray irradiation has been performed, it notifies the control unit 204 of it. Upon receiving the notification, the control unit 204 controls the sensor unit 201, the sensor driving unit 202, and the reading unit 203 to accumulate, in the sensor unit 201, charges by X-rays and generate an image by reading out the charges, similarly to the X-ray synchronization imaging mode in the first embodiment.

FIG. 12 shows an internal processing procedure according to the second embodiment. FIG. 12 shows the procedure by changing processing associated with imaging to processing in the X-ray irradiation detection mode based on FIG. 3. Steps S301 and S308 of FIG. 12 are the same as in FIG. 3A. Interrupt processing is the same as in FIG. 3B. A description of these processes will be omitted and processes from step S601 will be described below.

Before execution of step S601, the X-ray imaging apparatus 101 is activated and preparation for shifting to imaging is complete. In step S601, the control unit 204 determines whether a request to shift to imaging in the X-ray irradiation detection mode has been issued. If the request has been issued, the control unit 204 advances the process to step S602. This embodiment assumes imaging in the X-ray irradiation detection mode. However, an arrangement of switching between the X-ray irradiation detection mode and the X-ray synchronization imaging mode described in the first embodiment can be adopted. Processing for performing the determination operation may be implemented before step S601. In an example, the request to shift to the X-ray irradiation detection mode is given as an imaging sequence start instruction or the like from an imaging console 102 corresponding to the X-ray imaging apparatus 101.

In step S602, the control unit 204 performs preparation processing such as current supply or activation of functional units to shift to the X-ray irradiation detection mode. After that, in step S603, the control unit 204 notifies the user of the start of the X-ray irradiation detection mode by light or a sound. In step S604, the control unit 204 sets the X-ray imaging apparatus 101 in an X-ray irradiation waiting state in the X-ray irradiation detection mode, and executes X-ray irradiation detection by the X-ray irradiation detecting unit 501 while executing an idle readout operation, as described above.

In step S605, the control unit 204 determines whether a time-out of an X-ray irradiation detection time has occurred. As described above, in some X-ray detection methods, a very long time can be set. However, in consideration of actual use, processing is preferably stopped after a predetermined time as a preparation to a case in which the apparatus is left without X-ray irradiation. In addition, in a detection method in which the detection time is limited, a time-out time is naturally set. If it is determined that the irradiation waiting time has reached the time-out time, the control unit 204 ends the X-ray irradiation detection mode in step S606. The control unit 204 notifies, in step S607, the user of the end of the X-ray irradiation detection mode by a sound or light using a notification unit 208. After that, the process returns to step S308.

On the other hand, if it is determined in step S605 that no time-out time has elapsed, the process advances to step S608, and the control unit 204 determines whether X-ray irradiation has been detected. If it is determined that no X-ray irradiation has been detected, the process returns to step S604, and the loop of steps S604, S605, and S608 is repeated until a time-out occurs or X-ray irradiation is detected.

If it is determined in step S608 that X-ray irradiation has been detected, the process advances to step S609, and the control unit 204 ends the X-ray irradiation detection mode. In step S610, the control unit 204 uses the notification unit 208 to make a notification that X-ray irradiation has been detected, and also sets the sensor unit 201 in a charge accumulation enable state until X-ray irradiation ends, so as to form an image by emitted X-rays. This embodiment has explained the processing in step S610 as processing using a method of using, as a unit for detecting the entrance of X-rays, the sensor unit 201 used to acquire an image. If the X-ray irradiation detection method uses no sensor unit 201, the sensor unit 201 may be preset in the charge accumulation enable state, and only an X-ray irradiation detection notification may be performed in step S610. Subsequently, when X-ray irradiation ends, the process advances to step S611 to read out an image, similarly to X-ray synchronization imaging. The processing in step S611 is as described in steps S305 and S306.

Note that if the user is to be notified of serious contents of an error and it is impossible to capture an image in such state, a method of stopping the processing itself concerning imaging and making a notification by a sound of an arbitrary frequency by prioritizing an error notification may be performed. Furthermore, a method can be used in which sound-production requests are ranked in advance, and one of the above-described methods is selected to make a notification in accordance with the rank of the generated sound-production request.

The second embodiment has been described above. By implementing the apparatus in this form, it is possible to suppress the influence of sound production on X-ray irradiation detection even if a sound-production component is made to produce a sound during a period associated with X-ray irradiation detection. By using a notification sound of a specific frequency determined by the frequency of a sampling operation for detecting X-ray irradiation, an imaging apparatus having a function of detecting X-ray irradiation by itself suppresses an operation error led by the influence of noise caused by sound production.

Third Embodiment

Each of the first and second embodiments has explained the arrangement in which the imaging console 102 exists in the environment at the timing of imaging. The third embodiment will describe an arrangement in which an X-ray imaging apparatus 101 and an X-ray generating apparatus 108 perform imaging, and an imaging console 102 can be separated from the X-ray imaging apparatus 101 at the timing of imaging. In this specification, an operation mode of performing imaging in a state in which communication with the imaging console 102 is disabled will be referred to as a console-less mode hereinafter. More specifically, the X-ray imaging apparatus 101 is in a mode in which an X-ray image is accumulated in an internal storage unit 205 without being transferred to the imaging console 102 for each imaging operation.

FIGS. 13A and 13B each show an X-ray imaging system according to the third embodiment. FIG. 13A shows an arrangement before or after imaging, and FIG. 13B shows an arrangement during imaging. In the arrangement during imaging, the X-ray imaging apparatus 101, the X-ray generating apparatus 108, components associated with it, and an object 110 are used to perform imaging. Note that FIGS. 13A and 13B each show the X-ray generating apparatus 108 of a stationary type in an imaging room or the like but a movable set or an apparatus for mobile which is formed by arranging all the components on a cart may be used. The apparatus assumes an operation in which upon acquiring images during imaging, the X-ray imaging apparatus 101 accumulates the X-ray images in the internal storage unit 205, and collectively outputs them to the imaging console 102 such as a corresponding PC after imaging.

To implement such imaging operation, before imaging, the imaging console 102 and the X-ray imaging apparatus 101 are connected wirelessly or via a cable to, for example, make settings concerning one or both of imaging and the operation of the X-ray imaging apparatus 101. After the end of imaging, it is necessary perform processing of transferring images to the imaging console 102. FIG. 13A shows this state. FIG. 13A shows a state in which the components are connected via a cable but the components may be connected wirelessly. The components of the X-ray imaging apparatus 101 are the same as those in the second embodiment. The storage unit 205 for accumulating captured X-ray images may have a larger capacity.

The above-described arrangement according to the third embodiment has no mechanism for synchronization with the X-ray generating apparatus 108 in actual imaging, unlike the first embodiment, and it is necessary to perform imaging in the X-ray irradiation detection mode described in the second embodiment. Furthermore, since there is no imaging console 102 at the time of imaging, a requirement to notify the user of state transition by only the X-ray imaging apparatus 101 becomes high by increasing the number of times the X-ray imaging apparatus 101 returns a response to a user operation.

Figure 12A:
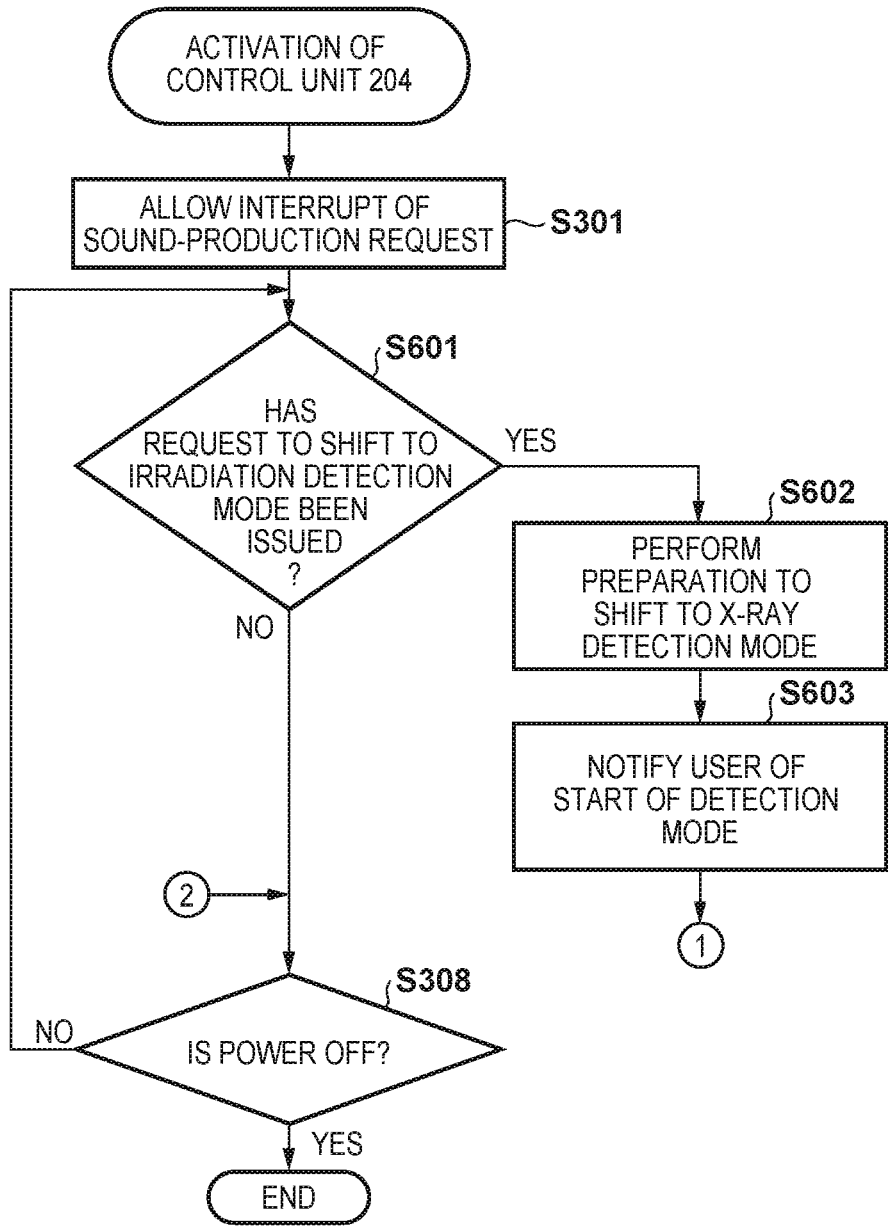
FIGS. 12A and 12B are flowcharts illustrating X-ray imaging processing at the time of an X-ray irradiation detection mode.
Figure 12B:
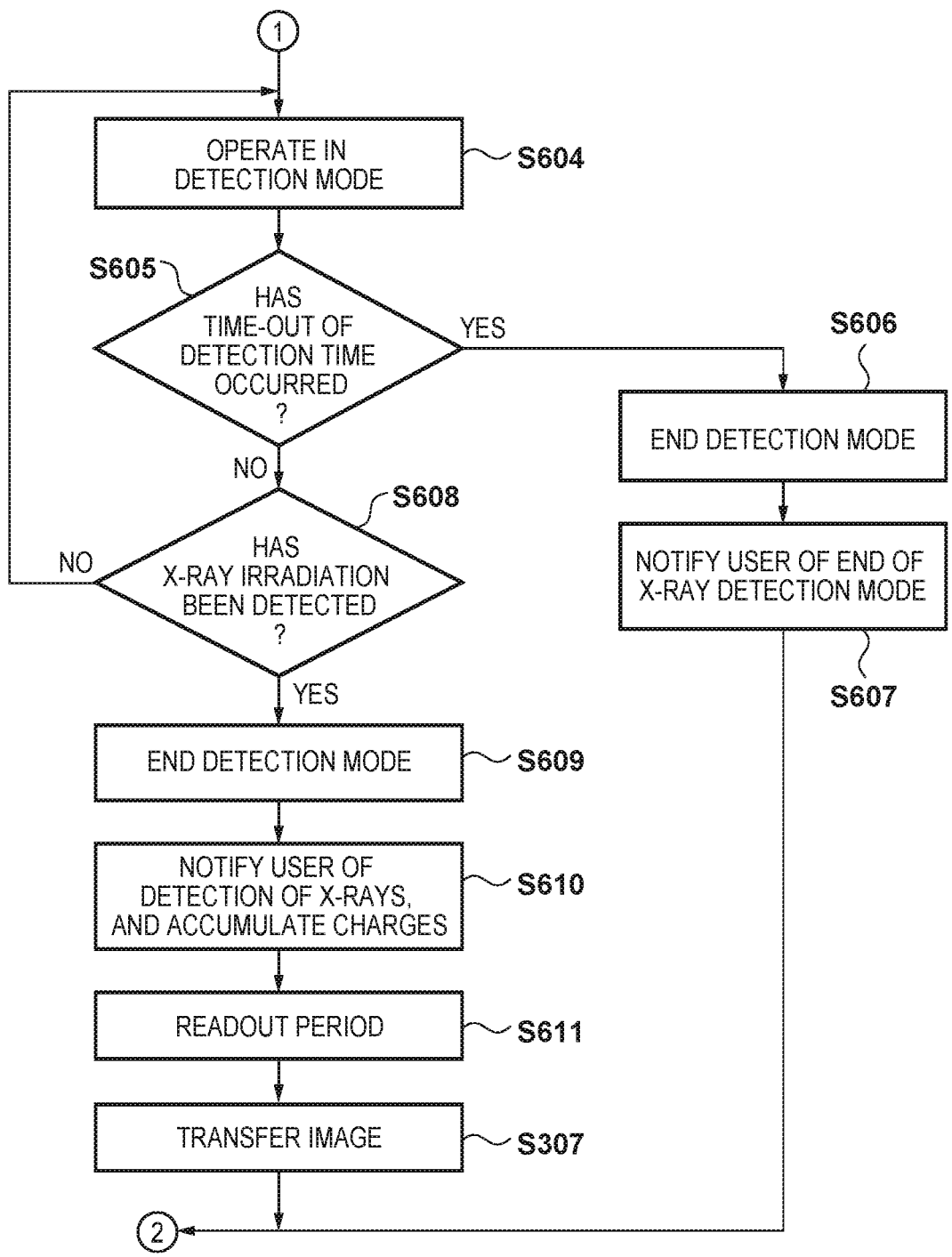
Figure 14:
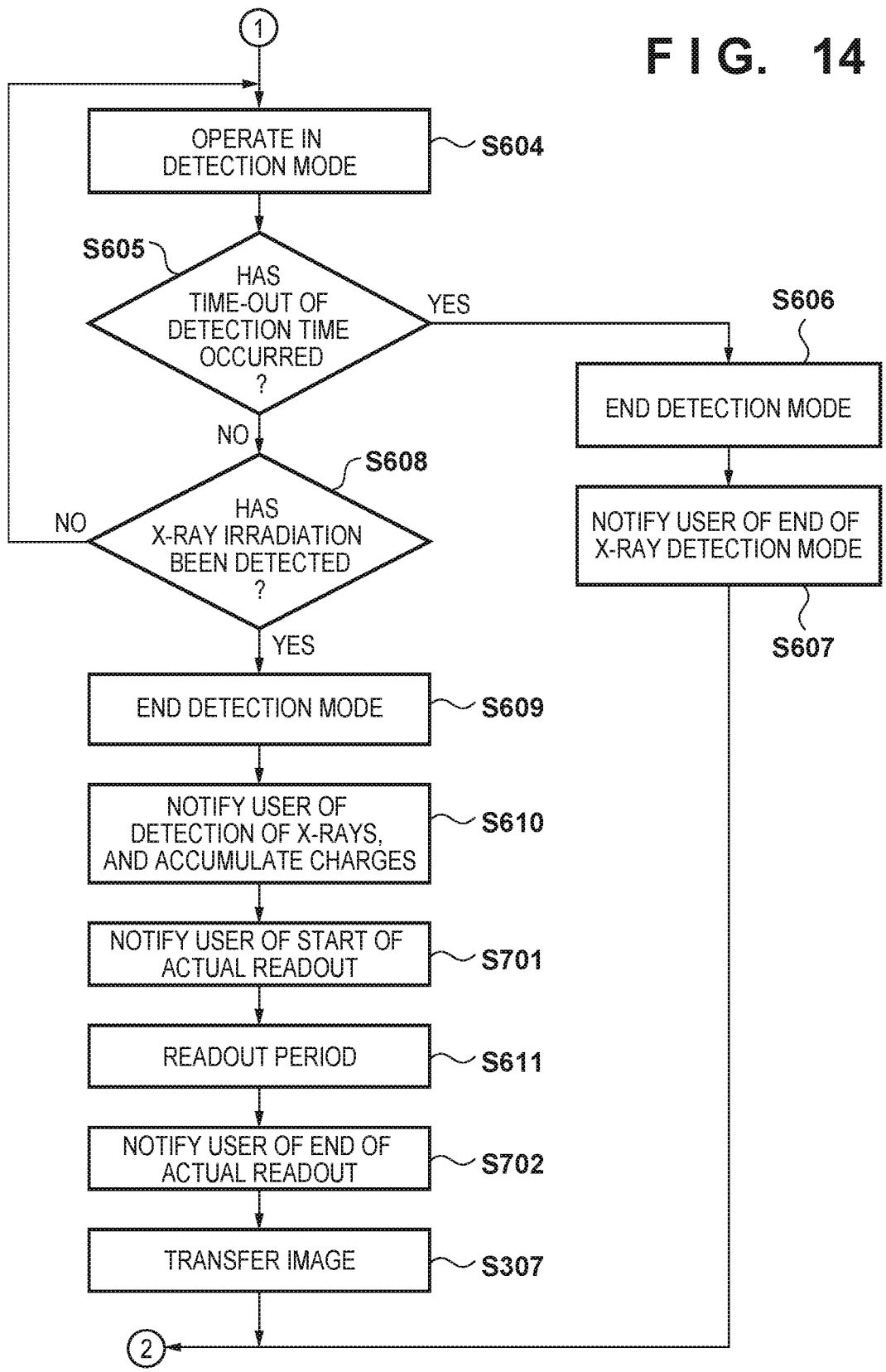
FIG. 14 is a flowchart illustrating X-ray imaging processing at the time of the console-less mode.

FIG. 14 shows an imaging procedure in this arrangement. FIG. 14 is a flowchart obtained by adding steps S701 and S702 to the flowchart (FIG. 12B) of the second embodiment. In the process of the third embodiment, among the processes of the second embodiment shown in FIGS. 12A and 12B, FIG. 12B is replaced by FIG. 14. Interrupt processing associated with a sound can be performed at any time from both the imaging console 102 and the main body of the X-ray imaging apparatus 101 in the first and second embodiments. In the third embodiment, however, a period during which settings can be changed from the imaging console 102 is limited. More specifically, the period is limited to periods during which the imaging console 102 and the X-ray imaging apparatus 101 are connected before and after imaging. Note that a condition under which interrupt processing can be performed by an operation from the main body of the X-ray imaging apparatus 101 is the same as in the second embodiment.

In step S601, in the second embodiment, the presence of a mode shift request is determined based on an instruction from the imaging console 102. The present invention, however, is not limited to this. For example, a method of determining a shift request in response to a user input to an operation unit 207 of the main body or disconnection from the imaging console 102 may be used. Furthermore, if the same apparatus uses the console-less mode described in this embodiment and the operable mode described in the first and second embodiments by switching between the console-less mode and the operable mode, switching acceptance processing may be added before step S601.

The difference from the second embodiment is addition of steps S701 and S702. In each step, a notification that the state is to transit or has transited is made before or after the charge accumulation and actual readout period. As described above, since the form of this embodiment includes no imaging console 102 in an imaging environment, it is desirable to increase the opportunity of notifying the user of the state of the X-ray imaging apparatus 101. Accordingly, steps S701 and S702 correspond to processing of increasing the opportunity of making a notification concerning the state and operation before and after the readout period (step S611). Note that since a sound is used to make a notification in steps S701 and S702 before the start of the readout period and after the end of the readout period, the above-described limitation of the fundamental frequency is not imposed. On the other hand, as a sound to notify the user of insufficiency of the residual amount of the battery or disconnection of communication, which can be generated at an arbitrary timing including the X-ray irradiation detection or the readout period, a sound which satisfies the condition of the fundamental frequency described in the first or second embodiment is used.

As described above, according to the third embodiment, even in a status in which there is no imaging console 102, the opportunity of notifying the user of the state of the X-ray imaging apparatus 101 and the contents of the notification can be prevented from decreasing. Even if the sound-production component is made to produce a sound during a period associated with X-ray irradiation detection and readout, it is possible to suppress the influence of sound production on X-ray irradiation detection and an image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-099049, filed May 17, 2016, which is hereby incorporated by reference herein in its entirety.

What is claimed is:

1. A radiation imaging apparatus, comprising:
  a sensor unit including a detector array in which a plurality of detecting elements each configured to detect emitted radiation are arranged and a signal readout unit that reads out signals in units of rows from a plurality of detecting elements of the detector array; and
  a notification unit configured to make a notification by a sound, wherein the sound produced from the notification unit has a fundamental frequency based on a readout frequency of signals in the sensor unit in which readout of signals in the units of rows is being performed by the signal readout unit.

2. The apparatus according to claim 1, wherein the sound produced from the notification unit has a fundamental frequency based on the number of rows of a predetermined area of an image read out from the sensor unit and a readout frequency of signals of each row.

3. The apparatus according to claim 2, wherein when a fundamental frequency fa of the sound produced from the notification unit satisfies a condition given by:

$$fa \leq fs/L \text{ for } fa \leq fs/2$$

$$fa \geq (L-1) \times fs/L \text{ for } fa > fs/2$$

where fs represents the readout frequency of the signals of each row from the sensor unit and L (L≥2) represents the number of rows of the predetermined area of the image read out from the sensor unit.

4. The apparatus according to claim 2, wherein the predetermined area is the whole or part of the image read out from the sensor unit.

5. The apparatus according to claim 1, wherein a sound having the fundamental frequency based on the readout frequency is set as a sound corresponding to a notification of a specific event.

6. The apparatus according to claim 5, further comprising:
a setting unit configured to set a correspondence between each of a plurality of events to be notified and a sound for a notification, wherein
a correspondence with a sound which does not have the fundamental frequency based on the readout frequency is prohibited from being set for the specific event among the plurality of events.

7. The apparatus according to claim 5, wherein the specific event includes insufficiency of a residual amount of a battery.

8. The apparatus according to claim 5, wherein the specific event includes occurrence of disconnection of communication.

9. A radiation imaging apparatus, comprising:
a sensor unit including a detector array in which a plurality of detecting elements each configured to detect emitted radiation are arranged and a signal readout unit that reads out signals in units of rows from a plurality of detecting elements of the detector array;
a notification unit configured to make a notification by a sound; and
a detecting unit configured to detect radiation irradiation to the sensor unit by sampling a current value flowing through a bias wiring connected to the plurality of detecting elements of the sensor unit in which readout of signals in the units of rows is being performed by the signal readout unit, wherein
a fundamental frequency of a sound produced from the notification unit satisfies a condition of being not higher than ½ of a frequency of sampling of the current value performed by the detecting unit.

10. The apparatus according to claim 9, wherein the detecting unit performs correlated double sampling by performing sampling at a timing of reading out signals of each row from the sensor unit for idle readout and a timing during the readout, and a fundamental frequency fa of a notification sound produced from the notification unit satisfies a condition given by fa≤fs
where fs represents a readout frequency of the signals of each row for the idle readout.

11. The apparatus according to claim 10, wherein in the correlated double sampling, a current value sampled at the time of execution of readout of the signals of each row from the sensor unit and an average value of two current values sampled before and after the readout are used.

12. A radiation imaging apparatus, comprising:
a sensor unit in which a plurality of detecting elements each configured to detect emitted radiation are arranged;
a notification unit configured to make a notification by a sound; and
a detecting unit including a bandpass filter for reducing noise, said detecting unit being configured to detect radiation irradiation to the sensor unit by sampling a current value flowing through a bias wiring of the sensor unit, wherein
a condition given by $$fa < fl \text{ or } fa > fh \text{ for } fa \leq fs/2$$

$$fs - fa < fl \text{ or } fs - fa > fh \text{ for } fa > fs/2$$

is satisfied where fa represents a fundamental frequency of the sound produced from the notification unit, fs represents a frequency of sampling by the detecting unit, and fl to fh represent a frequency band which the bandpass filter passes.

13. A control method for a radiation imaging apparatus including a sensor unit having a sensor array in which a plurality of detecting elements each configured to detect emitted radiation are arranged and a signal readout unit that reads out signals in units of rows from a plurality of detecting elements of the detector array, and a notification unit configured to make a notification by a sound, the method comprising the steps of:
detecting occurrence of an event to be notified; and
causing the notification unit to execute sound production in response to the detection of the occurrence of the event, wherein
the sound produced from the notification unit has a fundamental frequency based on a readout frequency of signals in the sensor unit in which readout of signals in the units of rows is being performed by the signal readout unit.

14. The method according to claim 13, wherein the sound produced from the notification unit has a fundamental frequency based on the number of rows of a predetermined area of an image read out from the sensor unit and a readout frequency of signals of each row.

15. The method according to claim 14, wherein if at least the event is a specific event, the notification unit is caused to produce a sound whose fundamental frequency fa satisfies a condition given by $$fa \leq fs/L \text{ for } fa \leq fs/2$$

$$fa \geq (L-1) \times fs/L \text{ for } fa > fs/2$$

where fs represents the readout frequency of the signals of each row from the sensor unit and L (L≥2) represents the number of rows of the predetermined area of the image read out from the sensor unit.

16. A non-transitory computer-readable medium storing a program for causing a computer to execute the control method according to claim 13.

* * * * *